United States Patent [19]

Tatsuoka et al.

[11] Patent Number: 5,158,947

[45] Date of Patent: Oct. 27, 1992

[54] CONDENSED HETEROCYCLIC COMPOUNDS AND PSYCHOPHARMACEUTICAL COMPOSITION CONTAINING SAME

[75] Inventors: Toshio Tatsuoka, Nishinomiya; Kayoko Nomura; Makoto Shibata, both of Takatsuki; Masanori Kawai, Higashikurume, all of Japan

[73] Assignee: Suntory Limited, Osaka, Japan

[21] Appl. No.: 717,005

[22] Filed: Jun. 18, 1991

[30] Foreign Application Priority Data

Jun. 28, 1990 [JP] Japan .................................. 2-168555

[51] Int. Cl.$^5$ ................. A61K 31/555; C07D 281/10; C07D 267/14; C07D 243/14; C07D 223/116
[52] U.S. Cl. .................................... 514/211; 540/490; 540/508; 540/523; 514/213; 514/221
[58] Field of Search ................. 540/490, 508, 523; 514/211, 213, 221

[56] References Cited

FOREIGN PATENT DOCUMENTS 0376633 7/1990 European Pat. Off. ............ 514/211

OTHER PUBLICATIONS

Chemical Abstracts, vol. 111, No. 11, Sep. 11, 1989, Abstract No. 97194n, Czollner et al.
Chemical Abstracts, vol. 62, No. 8, Apr. 12, 1965, Abstract No. 9137c, Huckle et al.
Chemical Abstracts, vol. 88, No. 21, May 22, 1978, Abstract No. 145961r, Bagolini et al.

*Primary Examiner*—Robert T. Bond
*Attorney, Agent, or Firm*—Burns, Doane, Swecker & Mathis

[57] ABSTRACT

A condensed heterocyclic compound having the formula (I):

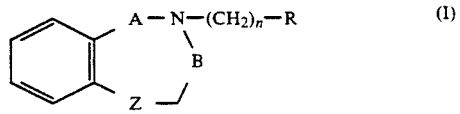

wherein A and B are both carbonyl groups of one thereof represents a methylene group and the other represents a carbonyl group; Z represents an oxygen atom, a sulfur atom, a substituted or unsubstituted nitrogen atom, or a methylene group; n is an integer of 2 to 6; and R represents a group having the following formula:

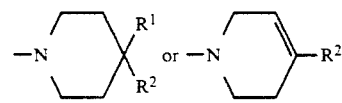

wherein $R^1$ represents a hydrogen atom or a hydroxyl group; $R^2$ represents a substituted or unsubstituted phenyl or 2-pyridyl group or salts thereof.

The compounds according to the present invention exhibit a strong affinity to the $\sigma$-receptor and are useful as psychopharmaceuticals.

12 Claims, No Drawings

CONDENSED HETEROCYCLIC COMPOUNDS AND PSYCHOPHARMACEUTICAL COMPOSITION CONTAINING SAME

BACKGROUND OF THE INVENTION

1. Field of the Invention

The present invention relates to a condensed heterocyclic compound and a psychopharmaceutical composition containing the same.

The condensed heterocyclic compounds and salts thereof according to the present invention show activities specific to the $\sigma$-receptor, and therefore, are effective as remedies for treating psychoneurosis.

2. Description of the Related Art

The principal conventionally developed remedies for treating psychosis are $D_2$-receptor antagonists such as butyrophenone derivatives represented by Haloperidol, phenothiazine, and thioxanthine, owing to the presence of dopamine in the brain.

Nevertheless, many cases have been known which cannot be improved by the use of these $D_2$-receptor antagonists, and it is known that the use thereof is accompanied by side-effects such as extrapyramidal tract disorders. Accordingly, there is a need for the development of a specific remedy for treating psychosis, which is not accompanied by side-effects.

In this connection, it recently has been proved that the $\sigma$-receptor, which is a subtype of the opioid receptor, is closely involved in the development of various symptoms of psychosis, and remedies have been developed for treating psychosis based on the $\sigma$-receptor antagonism, as represented by Rimcazole and BMY 14802 having the following structures, respectively.

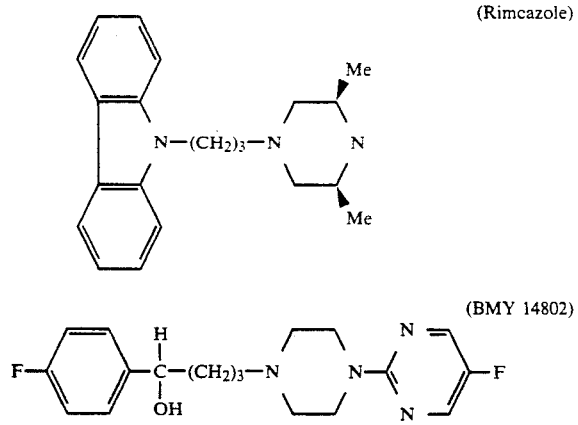

Nevertheless, the antipsychotic effect of these Rimicazole and BMY 14802 is inferior to those of existing remedies such as Haloperidol, and as a cause thereof, it is considered that the $\sigma$-receptor antagonism thereof is inferior to those of existing remedies such as Haloperidol.

SUMMARY OF THE INVENTION

Accordingly, the objects of the present invention are to eliminate the above-mentioned disadvantages of the prior art and to provide a novel compound having a strong affinity to the $\sigma$-receptor and a low affinity to the $D_2$-receptor and a psychopharmaceutical composition containing the same.

Other objects and advantages of the present invention will be apparent from the following description.

In accordance with the present invention, there is provided a condensed heterocyclic compound having the formula (I):

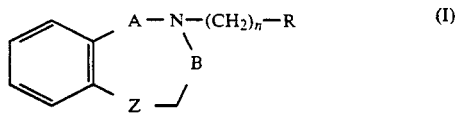

wherein A and B are both carbonyl groups or one thereof represents a methylene group and the other represents a carbonyl group; Z represents an oxygen atom, a sulfur atom, an unsubstituted or substituted imino group, or a methylene group; n is an integer ranging from 2 to 6; and R represents a group having the following formula:

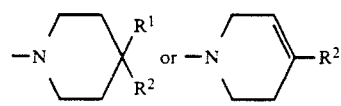

wherein $R^1$ represents a hydrogen atom or a hydroxyl group; $R^2$ represents a substituted or unsubstituted phenyl or 2-pyridyl group or salts thereof as well as a psychotropic drug containing the same as an effective component.

In accordance with the present invention, there is also provided a psychopharmaceutical composition comprising the above-mentioned a condensed heterocyclic compound having the formula (I) or a pharmacologically acceptable salt thereof, as an effective component, and a carrier therefor.

DESCRIPTION OF THE PREFERRED EMBODIMENTS

The present inventors conducted intensive studies into the developing of a pharmaceutically active compound having a stronger affinity for the $\sigma$-receptor and a lower affinity for the $D_2$-receptor, and thus a higher selectivity to the $\sigma$-receptor, and as a result, found that the compounds having the above-mentioned formula (I) and salts thereof show a strong affinity for the $\sigma$-receptor and a low affinity for the $D_2$-receptor, and thus completed the present invention.

The typical examples of the substituent in the substituted imino group in the formula (I) of the compounds according to the present inventions are $C_{1-5}$ alkyl group (for example, methyl, ethyl, propyl, butyl and pentyl group), aryl group (for example, phenyl, benzyl and phenethyl group) and heterocyclic group (for example, pyridyl group).

The preferable compound (I) according to the present invention are 4-(4-(4-phenyl)-1-piperidnyl) butyl-2,3,4,5-tetrahydro-1,4-benzodiazepine-3,5-dione (A,B-=carbonyl group, Z=imino group, n=4, R=piperidinyl group, $R^1$=hydrogen atom, $R^2$=phenyl group), 4-(5-(4-phenyl)-1-piperidinyl)pentyl-2,3,4,5-tetrahydro-1,4-benzoxazepin-5-one (A=carbonyl group, B=methylene group, Z=oxygen atom, n=5, R=piperidinyl group, $R^1$=hydrogen atom, $R^2$=phenyl group) and 2-(5-(4-(chlorophenyl)-1-piperidinyl)pentyl-1,3,4,5-tetrahydro-2-benzazepine-1,3-dione (A,B=carbonyl group, Z=methylen group, n=5, R=piperidinyl group, $R^1$=hydrogen atom, $R^2$=4-chlorophenyl group).

The compounds having the above-mentioned formula (I) according to the present invention can be prepared, for example, by the following methods:

1) Preparation of Intermediate Compounds (II):

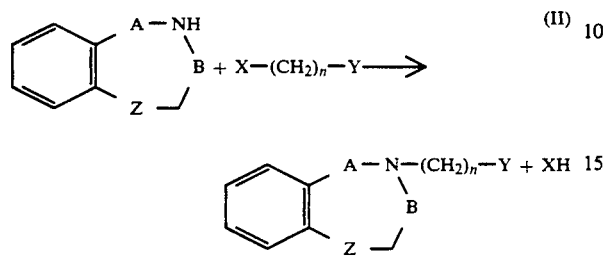

wherein A, B, Z and n are the same as defined above and X and Y may be the same or different and each represents a halogen atom.

2) Preparation of Final Compounds:

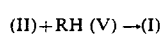

(wherein R is the same as defined above).

More specifically, a compound represented by the following general formula (Ia):

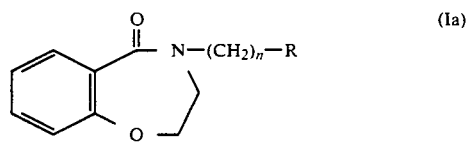

i.e., a compound of the formula (I), wherein A is a carbonyl group, B is a methylene group and Z is an oxygen atom, can be prepared by forming a compound having the following formula (III):

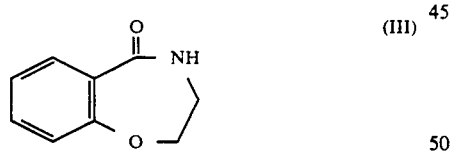

according to the method disclosed in the article of G. S. Sidhu, G. Thyagarajan and U. T. Bhalerao (J. Chem. Soc. (C), 1966, p. 969), reacting same with a dibromoalkane to form a compound having the formula (IV):

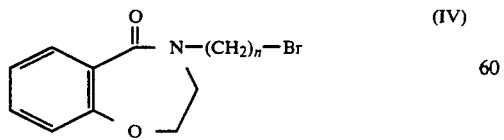

and then condensing the resulting compound with an amine derivative of the formula (V) in the usual manner.

A compound having the following general formula (Ib):

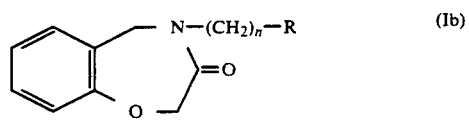

i.e., a compound of the formula (I) wherein A is a methylene group, B is a carbonyl group and Z is an oxygen atom, can be prepared by forming a compound having the following formula (VI):

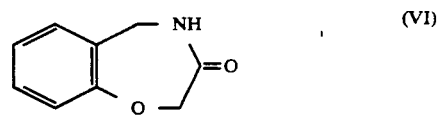

according to the method disclosed in the article of Kost. A. N., Stankevicius, A. (Khim. Geterotsiki. Soedin., 1971, 7 (9), p. 1288), reacting it with a dibromoalkane to give a compound having the following general formula (VII)

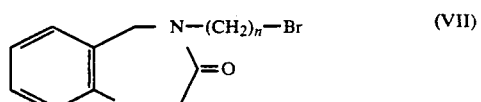

and then condensing the resulting compound with an amine derivative (V) in a usual manner. A compound having the following general formula (Ic):

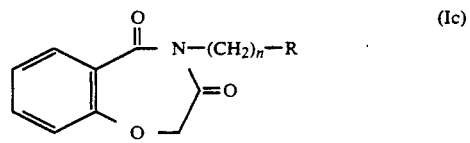

i.e., a compound of the formula (I) wherein A and B each represents a carbonyl group and Z is an oxygen atom, can be prepared by forming a compound having the following formula (VIII):

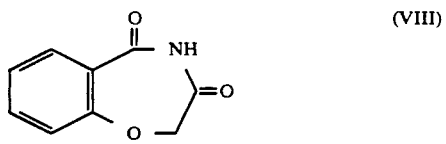

according to the method disclosed in the article of A. Cattaneo, P. Galimberti, M. Melandri (Boll. Chim. Farm., 1963, 102, p. 541), reacting it with a dibromoalkane to give a compound having the following general formula (IX)

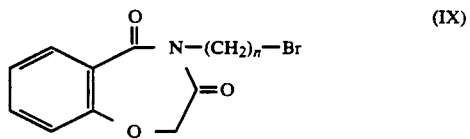

and then condensing the resulting compound with an amine derivative (V) in a usual manner.

The compound having the general formula (I) and pharmacologically acceptable salts thereof (such as hydrochlorides, sulfates, nitrates, hydrobromides, phosphates, methanesulfonates, p-toluenesulfonates, acetates, oxalates, malonates, succinates, tartrates, maleates, fumarates, lactates, citrates and malates) according to the present invention can be administered alone, or if necessary and desirable, in combination with other commonly pharmacologically acceptable additives such as carriers, excipients and diluents in desired shapes such as tablets, capsules, powder, liquids, injectable liquids, and suppositories through oral or parenteral routes. Examples of such carriers or diluents are polyvinylpyrrolidone, gum arabic, gelatin, sorbit, cyclodextrin, tragacanth, magnesium stearate, talc, polyethylene glycol, polyvinyl alcohol, silica, lactose, crystalline cellulose, sugar, starches, potassium phosphate, vegetable oils, calcium carboxymethyl cellulose, sodium laurylsulfate, water, ethanol, glycerin, mannitol, and syrup.

The concentration of the compound of the formula (I) in the pharmaceutical composition is not restricted, but is generally from 1 to 100% by weight, preferably 10 to 90% by weight. Moreover, the dose thereof is not critical, but is generally from 0.01 to 1,000 mg/day/man, preferably 0.1 to 500 mg/day/man. The frequency of the administration is usually 1 to 3 times per day.

EXAMPLES

The present invention will now be further illustrated by, but is by no means limited to, the following Reference Examples, Examples and Test Examples.

REFERENCE EXAMPLE 1 Preparation of 4-(5-bromopentyl)-2,3,4,5-tetrahydro-1,4-benzoxazepin-5-one

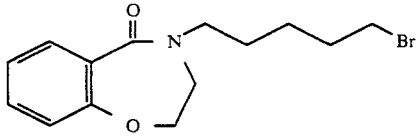

In 20 ml of dimethylformamide (DMF) was dissolved 100 mg of 2,3,4,5-tetrahydro-1,4-benzoxazepin-5-one, and the solution then ice-cooled. Then, to the resulting solution were added 0.251 ml (3 equivalents) of 1,5-dibromopentane and 29.4 mg (1.2 equivalent) of a 60% sodium hydride oil dispersion, and the mixture was stirred for one hour with ice-cooling. The reaction solution was poured into a citric acid aqueous solution and extracted with ethyl acetate, and the ethyl acetate phase was washed with an aqueous saturated sodium chloride solution, dried over anhydrous magnesium sulfate, and then filtered. The filtrate was then concentrated and the resulting residue was purified by silica gel column chromatography (eluent: hexane/ethyl acetate (8:2)) to give 124 mg (yield: 65.0%) of the title compound.

REFERENCE EXAMPLE 2 Preparation of 4-(5-bromopentyl)-2,3,4,5-tetrahydro-1,4-benzoxazepin-3-one

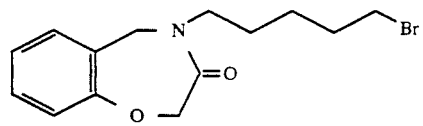

In 20 ml of DMF was dissolved 100 mg of 2,3,4,5-tetrahydro-1,4-benzoxazepin-3-one and the solution then ice-cooled. Then, to the resulting solution were added 0.125 ml (1.5 equivalent) of 1,5-dibromopentane and 29.4 mg (1.2 equivalent) of a 60% sodium hydride oil dispersion and the mixture was stirred for 1.5 hour with ice-cooling. Thereafter, the reaction solution was reacted and/or treated and purified in the same manner as in Reference Example 1 to give 133 mg (yield: 69.5%) of the title compound.

REFERENCE EXAMPLE 3 Preparation of 4-(5-bromopentyl)-2,3,4,5-tetrahydro-1,4-benzothiazepine-3,5-dione

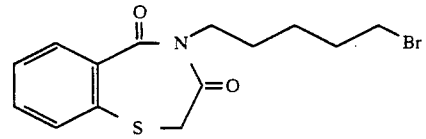

In 20 ml of DMF was dissolved 102 mg of 2,3,4,5-tetrahydro-1,4-benzothiazepine-3,5-dione and the solution then ice-cooled. Then, to the resulting solution were added 0.116 ml (1.5 equivalent) of 1,5-dibromopentane and 27.4 mg (1.2 equivalent) of a 60% sodium hydride oil dispersion and the mixture was stirred for 2 hours with ice-cooling. Thereafter, the reaction solution was reacted and/or treated and purified in the same manner as in Reference Example 1 to give 79.2 mg (yield: 42.4%) of the title compound.

REFERENCE EXAMPLE 4 Preparation of 4-(5-bromopentyl)-2,3,4,5-tetrahydro-1,4-benzodiazepine-3,5-dione

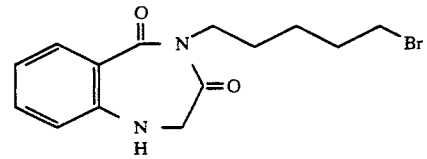

In 10 ml of dimethylformamide (DMF) was dissolved 100 mg of 2,3,4,5-tetrahydro-1,4-benzodiazepine-3,5-dione and the solution then ice-cooled. Then, to the resulting solution were added 0.116 ml (1.5 equivalent) of 1,5-dibromopentane and 27.3 mg (1.2 equivalent) of a 60% sodium hydride oil dispersion and the mixture was stirred for 2 hours with ice-cooling. The reaction solution was poured into ice-cooled water containing citric acid, made alkaline with sodium hydrogen carbonate, and extracted with ethyl acetate. The ethyl acetate phase was then washed with an aqueous saturated sodium chloride solution and dried over anhydrous magnesium sulfate. The product was purified in the same manner as in Reference Example 1 to give 97.5 mg (yield: 52.8%) of the title compound.

REFERENCE EXAMPLE 5 Preparation of 2-(5-bromopentyl)-1,3,4,5-tetrahydro-2-benzazepine-1,3-dione

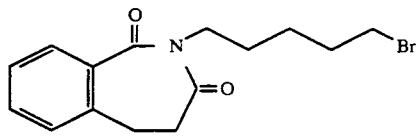

In 20 ml of DMF was dissolved 100 mg of 1,3,4,5-tetrahydro-2-benzazepine-1,3-dione and the solution then ice-cooled. Then, to the resulting solution were added 0.117 ml (1.5 equivalent) of 1,5-dibromopentane and 27.4 mg (1.2 equivalent) of a 60% sodium hydride oil dispersion and the mixture was stirred for 1.5 hour with ice-cooling. Thereafter, the reaction solution was reacted and/or treated and purified in the same manner as in Reference Example 1 to give 109 mg (yield: 58.9%) of the title compound.

Physical data of the compounds prepared in Reference Examples 1 to 5 are summarized in Table 1.

REFERENCE EXAMPLE 6 Preparation of 4-(4-bromobutyl)-2,3,4,5-tetrahydro-1,4-benzoxazepin-5-one

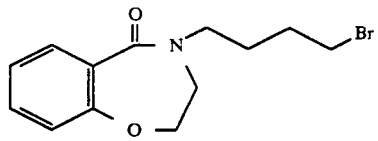

The same procedures as used in Reference Example 1 were repeated except that 1,4-dibromobutane was substituted for 1,5-dibromopentane to give the title compound.

TABLE I

| Ref. Ex. No. | m.p. | IR (cm$^{-1}$) | | NMR (δ ppm) | Mass |
|---|---|---|---|---|---|
| 1 | Oily product | 2930 | 2870 | 1.48–1.96(m, 6H) | HiMs |
|   |   | 1640 | 1600 | 3.43(t, 2H, J=6.6Hz), 3.50(t, 2H, J=5.3Hz) | Calcd. 311.0520 |
|   |   | 1470 | 1420 | 3.60–3.65(m, 2H) | Obsd. 311.0504 |
|   |   | 1360 | 1320 | 4.37(t, 2H, J=5.3Hz) |   |
|   |   | 1285 | 1210 | 7.00(d, 1H, J=7.9Hz) |   |
|   |   | 1110 | 1045 | 7.16(t, 1H, J=7.9Hz) |   |
|   |   | 875  | 805  | 7.41(dt, 1H, J=2.0Hz & 7.9Hz) |   |
|   |   | 790  | 760  | 7.80(dd, 1H, J=2.0Hz & 7.9Hz) |   |
|   |   | 705  |      |   |   |
| 2 | Oily product | 2930 | 2870 | 1.38–1.92(m, 6H) | HiMs |
|   |   | 1670 | 1640 | 3.37(t, 2H, J=6.6Hz) | Calcd. 311.0520 |
|   |   | 1580 | 1495 | 3.55(t, 2H, J=7.3Hz) | Obsd. 311.0536 |
|   |   | 1460 | 1435 | 4.47(s, 2H) |   |
|   |   | 1350 | 1310 | 4.69(s, 2H) |   |
|   |   | 1230 | 1220 | 7.03–7.33(m, 4H) |   |
|   |   | 1195 | 1115 |   |   |
|   |   | 1055 | 1025 |   |   |
|   |   | 845  | 760  |   |   |
|   |   | 700  |      |   |   |
| 3 | Oily product | 2920 | 2850 | 1.43–1.95(m, 6H) | HiMs |
|   |   | 1690 | 1640 | 3.40(t, 2H, J=6.6Hz) | Calcd. 341.0084 |
|   |   | 1580 | 1455 | 3.68(s, 2H) | Obsd. 341.0074 |
|   |   | 1430 | 1330 | 4.00(t, 2H, J=7.3Hz) |   |
|   |   | 1290 | 1260 | 7.37–7.49(m, 3H) |   |
|   |   | 1220 | 1105 | 8.16–8.20(m, 1H) |   |
|   |   | 1080 | 950  |   |   |
|   |   | 910  | 780  |   |   |
|   |   | 740  | 685  |   |   |
| 4 | 65–66° C. | 3350 | 2940 | 1.39–1.92(m, 6H) | HiMs |
|   |   | 2860 | 1700 | 3.78(t, 2H, J=6.6Hz) | Calcd. 324.0472 |
|   |   | 1620 | 1495 | 3.87–3.92(m, 2H) | Obsd. 324.0424 |
|   |   | 1430 | 1395 | 3.90(d, 2H, J=4.6Hz)4.87(t, 1H, J=4.6Hz) |   |
|   |   | 1360 | 1320 | 6.79(d, 1H, J=7.9Hz) |   |
|   |   | 1240 | 1155 | 6.95(dd, 1H, J=7.3Hz & 7.9Hz) |   |
|   |   | 1125 | 1105 | 7.35(ddd, 1H, J=1.3Hz & 7.3Hz & 7.9Hz) |   |
|   |   | 1020 | 980  | 8.25(dd, 1H, J=1.3Hz & 7.9Hz) |   |
|   |   | 860  | 785  |   |   |
|   |   | 755  | 700  |   |   |
| 5 | Oily product | 2950 | 2860 | 1.48–1.97(m, 6H) | HiMs |
|   |   | 1700 | 1645 | 2.99(s, 4H) | Calcd. 323.0520 |
|   |   | 1600 | 1455 | 3.40–3.45(m, 2H) | Obsd. 323.0472 |
|   |   | 1340 | 1315 | 4.00(t, 2H, J=7.3Hz) |   |
|   |   | 1265 | 1240 | 7.16(d, 1H, J=7.3Hz) |   |
|   |   | 1210 | 1115 | 7.33–7.48(m, 2H) |   |
|   |   | 1040 | 890  | 7.96(dd, 1H, J=1.3Hz & 7.9Hz) |   |
|   |   | 795  | 755  |   |   |
|   |   | 710  |      |   |   |

REFERENCE EXAMPLE 7 Preparation of 4-(4-bromobutyl)-2,3,4,5-tetrahydro-1,4-benzoxazepin-3-one

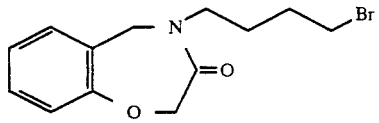

The same procedures as used in Reference Example 2 were repeated except that 1,4-dibromobutane was substituted for 1,5-dibromopentane to give the title compound.

REFERENCE EXAMPLE 8 Preparation of 4-(4-bromobutyl)-2,3,4,5-tetrahydro-1,4-benzoxazepin-3,5-dione

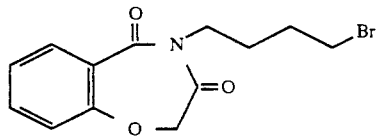

The same procedures as used in Reference Example 1 were repeated except that 2,3,4,5-tetrahydro-1,4-benzoxazepine-3,5-dione was substituted for 2,3,4,5-tetrahydro-1,4-benzoxazepin-3-one to give the title compound.

REFERENCE EXAMPLE 9 Preparation of 4-(4-bromobutyl)-2,3,4,5-tetrahydro-1,4-benzothiazepine-3,5-dione

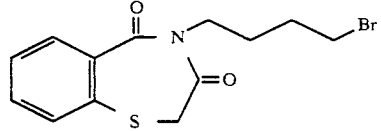

The same procedures as used in Reference Example 3 were repeated except that 1,4-dibromobutane was substituted for 1,5-dibromopentane to give the title compound.

REFERENCE EXAMPLE 10 Preparation of 4-(4-bromobutyl)-2,3,4,5-tetrahydro-1,4-benzothiazepine-3,5-dione

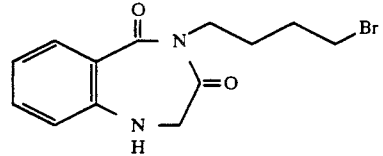

The same procedures as used in Reference Example 4 were repeated except that 1,4-dibromobutane was substituted for 1,5-dibromopentane to give the title compound.

REFERENCE EXAMPLE 11 Preparation of 1-methyl-4-(4-bromobutyl)-2,3,4,5-tetrahydro-1,4-benzothiazepine-3,5-dione

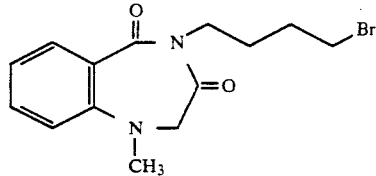

The same procedures as used in Reference Example 10 were repeated except that 1-methyl-2,3,4,5-tetrahydro-1,4-benzodiazepine-3,5-dione was substituted for 2,3,4,5-tetrahydro-1,4-benzothiazepine-3,5-dione to give the title compound.

REFERENCE EXAMPLE 12 Preparation of 2-(4-bromobutyl)-1,3,4,5-tetrahydro-2-benzazepine-1,3-dione

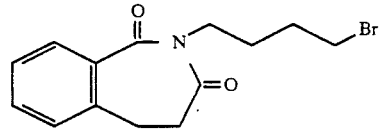

The same procedures as used in Reference Example 5 were repeated except that 1,4-dibromobutane was substituted for 1,5-dibromopentane to give the title compound.

REFERENCE EXAMPLE 13 Preparation of 4-(5-bromopentyl)-2,3,4,5-tetrahydro-1,4-benzoxazepine-3,5-dione

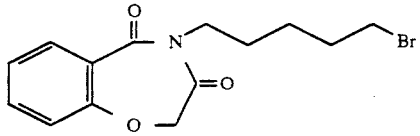

The same procedures as used in Reference Example 8 were repeated except that 1,5-dibromopentane was substituted for 1,4-dibromobutane to give the title compound.

EXAMPLE 1 Synthesis of 4-(4-(4-phenyl)-1-piperidinyl)butyl-2,3,4,5-tetrahydro-1,4-benzoxazepin-5-one

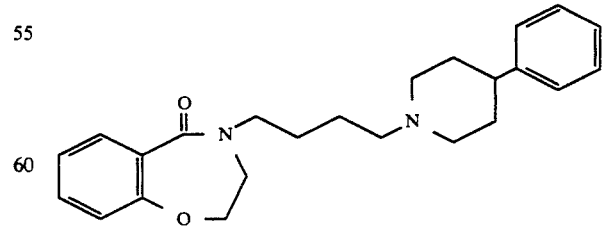

In 10 ml of dioxane was dissolved 49.8 mg of the compound obtained in Reference Example 6, 80.8 mg (3 equivalents) of 4-phenylpiperidine was added to the resulting solution, and the mixture was stirred at 110° C. for 3 hours with heating. The dioxane was distilled off, an aqueous solution of sodium hydrogen carbonate was added thereto, and the resulting solution was extracted with methylene chloride. The methylene chloride phase was washed with water, dried over anhydrous magnesium sulfate, and then filtered. The resulting filtrate was concentrated and the residue obtained was subjected to silica gel column chromatography (developing solution : ethyl acetate) to give 56.3 mg (yield: 89.1%) of the title compound. The hydrochloride of this compound was obtained by converting the compound into hydrochloride in the usual manner, and then recrystallizing the salt from methylene chloride-ether.

EXAMPLE 2 Synthesis of 4-(4-(4-(4-chlorophenyl)-1-piperidinyl)butyl)-2,3,4,5-tetrahydro-1,4-benzoxazepin-5-one

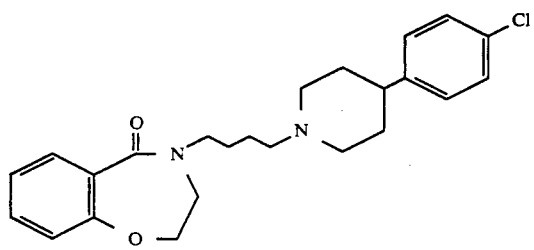

In 110 ml of dioxane was dissolved 61.3 mg of the compound prepared in Reference Example 6, then 121 mg (3 equivalents) of 4-(4-chlorophenyl)piperidine was added thereto, and the resulting mixture was stirred at 110° C. for 3 hours with heating. Thereafter, the same procedures for reaction, treatment and purification as used in Example 1 were repeated to give 76.9 mg (yield: 90.6%) of the title compound. The hydrochloride of this compound was obtained by converting the compound into hydrochloride in the usual manner, and then recrystallizing the salt from methylene chloride-ether.

EXAMPLE 3 Synthesis of 4-(4-(4-hydroxy-4-phenyl)-1-piperidinyl)butyl)-2,3,4,5-tetrahydro-1,4-benzoxazepin-5-one

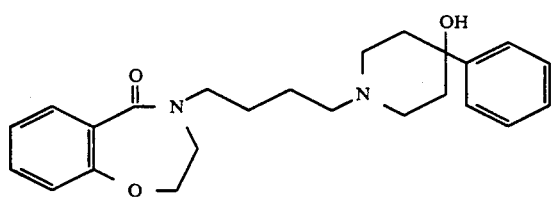

In 10 ml of dioxane was dissolved 119 mg of the compound prepared in Reference Example 6, then 212 mg (3 equivalents) of 4-hydroxy-4-phenylpiperidine was added thereto, and the resulting mixture was stirred at 100° C. for 2 hours with heating. Thereafter, the same procedures for reaction, treatment and purification as used in Example 1 were repeated to give 153 mg (yield: 97.2%) of the title compound. The hydrochloride of this compound was obtained by converting the compound into hydrochloride in the usual manner, and then recrystallizing the salt from methylene chloride-ether.

EXAMPLE 4 Synthesis of 4-(4-(4-phenyl)-1-piperidinyl)butyl)-2,3,4,5-tetrahydro-1,4-benzoxazepin-5-one

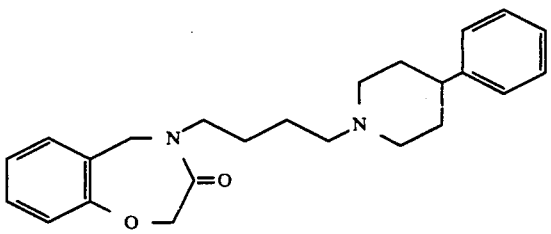

In 10 m l of dioxane was dissolved 20 mg of the compound prepared in Reference Example 7, then 32.5 mg (3 equivalents) of 4-phenylpiperidine was added thereto, and the resulting mixture was stirred at 100° C. for 5 hours with heating. Thereafter, the same procedures for reaction, treatment and purification as used in Example 1 were repeated to give 17.9 mg (yield: 70.5%) of the title compound. The hydrochloride of this compound was obtained by converting the compound into hydrochloride in the usual manner, and then recrystallizing the salt from methylene chloride-ether.

EXAMPLE 5 Synthesis of 4-(4-(4-chlorophenyl)-1-piperidinyl)butyl)-2,3,4,5-tetrahydro-1,4-benzoxazepin-3-one

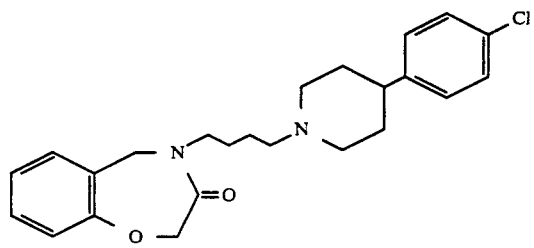

In 7 ml of dioxane 30.5 mg of the compound prepared in Reference Example 7, then 60 mg (3 equivalents) of 4-(4-chlorophenyl)piperidine was added thereto, and the resulting mixture was stirred at 110° C. for 4 hours with heating. Thereafter, the same procedures for reaction, treatment and purification as used in Example 1 were repeated to give 21.7 mg (yield: 51.4%) of the title compound. The hydrochloride of this compound was obtained by converting the compound into hydrochloride in the usual manner, and then recrystallizing the salt from methylene chloride-ether.

EXAMPLE 6 Synthesis of 4-(4-(4-hydroxy-4-phenyl)-1-piperidinyl)butyl-2,3,4,5-tetrahydro-1,4-benzoxazepin-3-one

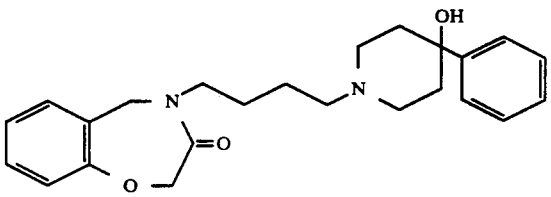

In 10 ml of dioxane was dissolved 45.0 mg of the compound prepared in Reference Example 7, then 80.3 mg (3 equivalents) of 4-hydroxy-4-phenylpiperidine was added thereto, and the resulting mixture was stirred at 110° C. for 4 hours with heating. Thereafter, the same procedures for reaction, treatment and purification as used in Example 1 were repeated to give 58.3 mg (yield: 98.0%) of the title compound. The hydrochloride of this compound was obtained by converting the compound into hydrochloride in the usual manner, and then recrystallizing the salt from methylene chloride-ether.

EXAMPLE 7 Synthesis of 4-(4-(4-(4-chlorophenyl)-4-hydroxy)-1-piperidinyl)-butyl-2,3,4,5-tetrahydro-1,4-benzoxazepin-3-one

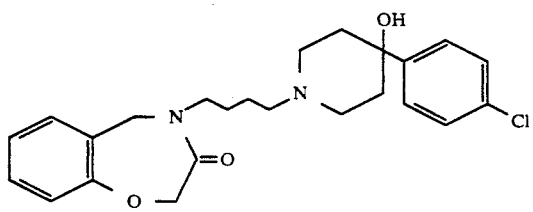

In 8 ml of dioxane was dissolved 47.0 mg of the compound prepared in Reference Example 7, then 100 mg (3 equivalents) of 4-(4-chlorophenyl)-4-hydroxypiperidine was added thereto, and the resulting mixture was stirred at 120° C. for 3 hours with heating. Thereafter, the same procedures for reaction, treatment and purification as used in Example 1 were repeated to give 61.2 mg (yield: 90.5%) of the title compound. The hydrochloride of this compound was obtained by converting the compound into hydrochloride in the usual manner, and then recrystallizing the salt from methylene chloride-ether.

EXAMPLE 8 Synthesis of 4-(4-(4-phenyl)-1-piperidinyl)butyl-2,3,4,5-tetrahydro-1,4-benzoxazepine-3,5-dione

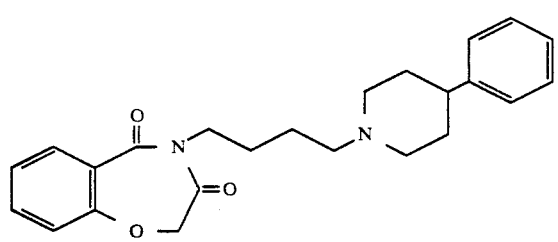

In 40 ml of dioxane was dissolved 1.30 g of the compound prepared in the Reference Example 8, 966 mg (1.5 equivalent) of 4-phenylpiperidine and 1.10 g (2 equivalents) of anhydrous potassium carbonate were added to the resulting solution, and the mixture was refluxed for 16 hours. The dioxane was distilled off under a reduced pressure, water and ethyl acetate were added to the resulting residue to perform a liquid-liquid separation, the ethyl acetate phase was dried over anhydrous magnesium sulfate, and then the solvent was distilled off under a reduced pressure. The residue was developed with ethyl acetate-hexane (9:1) using silica gel column chromatography to give 1.52 g (yield: 96.8%) of the title compound. The hydrochloride of this compound was obtained by converting the compound into hydrochloride in the usual manner, and then recrystallizing the salt from methylene chloride-ether.

EXAMPLE 9 Synthesis of 4-(4-(4-(4-chlorophenyl)-1-piperidinyl)butyl)-2,3,4,5-tetrahydro-1,4-benzoxazepine-3,5-dione

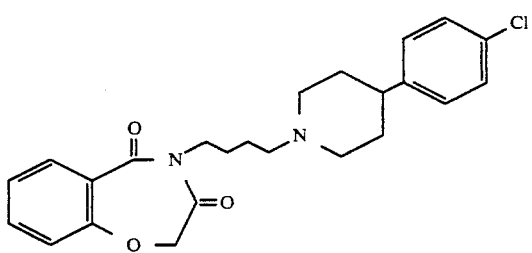

In 8 ml of dioxane was dissolved 20 mg of the compound prepared in Reference Example 8, then 37.6 mg (3 equivalents) of 4-(4-chlorophenyl)piperidine was added thereto, and the resulting mixture was stirred at 110° C. for 6 hours with heating. Thereafter, the same procedures for reaction, treatment and purification as used in Example 1 were repeated to give 19.1 mg (yield: 69.7%) of the title compound. The hydrochloride of this compound was obtained by converting the compound into hydrochloride in the usual manner, and then recrystallizing the salt from methylene chloride-ether.

EXAMPLE 10 Synthesis of 4-(4-(4-hydroxy-4-phenyl)-1-piperidinyl)butyl)-2,3,4,5-tetrahydro-1,4-benzoxazepine-3,5-dione

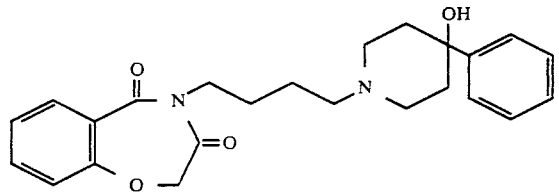

In 10 ml of dioxane was dissolved 114 mg of the compound prepared in Reference Example 8, then 194 mg (3 equivalents) of 4-hydroxy-4-phenylpiperidine was added thereto, and the resulting mixture was stirred at 120° C. for 3 hours with heating. Thereafter, the same procedures for reaction, treatment and purification as used in Example 1 were repeated to give 148 mg (yield: 99.0%) of the title compound. The hydrochloride of this compound was obtained by converting the compound into hydrochloride in the usual manner, and then recrystallizing the salt from methylene chloride-ether.

EXAMPLE 11 Synthesis of 4-(4-(4-(4-chlorophenyl)-4-hydroxy-1-piperidinyl)butyl-2,3,4,5-tetrahydro-1,4-benzoxazepine-3,5-dione

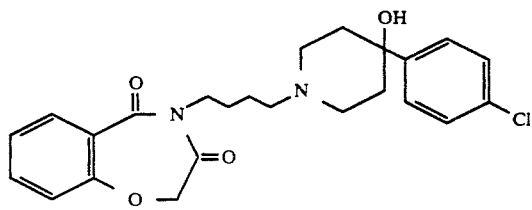

In 10 ml of dioxane was dissolved 48.7 mg of the compound prepared in Reference Example 8, then 99.0 mg (3 equivalents) of 4-(4-chlorophenyl)-4-hydrox-

EXAMPLE 12 Synthesis of 4-(4-(4-phenyl-1,2,3,6-tetrahydro)-1-pyridyl)butyl-2,3,4,5-tetrahydro-1,4-benzoxazepine-3,5-dione

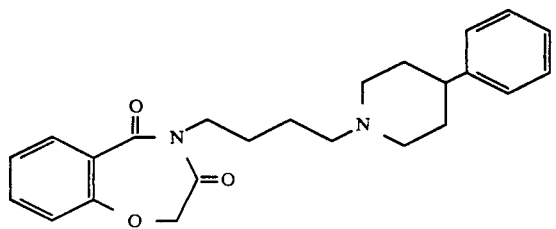

In 10 ml of dioxane was dissolved 218 mg of the compound prepared in Reference Example 8, then 318 mg (2.9 equivalents) of 4-phenyl-1,2,3,6-tetrahydropyridine was added thereto, and the resulting mixture was refluxed for 20 hours. Thereafter, the same procedures for reaction, treatment and purification as used in Example 1 were repeated to give 50 mg (yield: 18.2%) of the title compound. The hydrochloride of this compound was obtained by converting the compound into hydrochloride in the usual manner, and then recrystallizing the salt from methylene chloride-ether.

EXAMPLE 13 Synthesis of 4-(4-(4-(4-chlorophenyl)-1,2,3,6-tetrahydro-1-pyridyl)-butyl-2,3,4,5-tetrahydro-1,4-benzoxazepine-3,5-dione

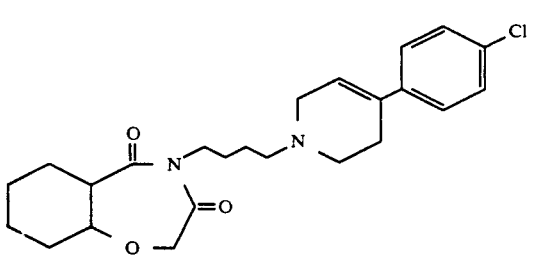

In 10 ml of dioxane was dissolved 50 mg of the compound prepared in Reference Example 8, then 93.0 mg (3 equivalents) of 4-(4-chlorophenyl)-1,2,3,6-tetrahydropyridine was added thereto, and the resulting mixture was stirred at 110° C. for 7 hours with heating. Thereafter, the same procedures for reaction, treatment and purification as used in Example 1 were repeated to give 23.0 mg (yield: 33.7%) of the title compound. The hydrochloride of this compound was obtained by converting the compound into hydrochloride in the usual manner, and then recrystallizing the salt from methylene chloride-ether.

EXAMPLE 14 Synthesis of 4-(4-(4-(2-pyridyl)-1-piperidinyl)butyl)-2,3,4,5-tetrahydro-1,4-benzoxazepine-3,5-dione

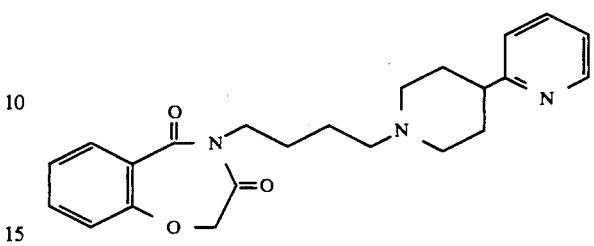

In 20 ml of dioxane was dissolved 326 mg of the compound obtained in Reference Example 8, 552 mg (2 equivalents) of 4-(2-pyridyl)piperidine.trifluoroacetate and 2.76 g (20 equivalents) of anhydrous potassium carbonate were added thereto, and the resulting mixture was refluxed for 8 hours. The dioxane was distilled off under a reduced pressure, a 0.5 N aqueous solution of sodium hydroxide was added to the resulting residue, the product was extracted with ethyl acetate, the ethyl acetate phase was dried over anhydrous magnesium sulfate, and then the solvent was distilled off under a reduced pressure. The residue obtained was subjected to silica gel column chromatography (developing solution: methylene chloride-methanol (9:1) to give 270 mg (yield: 68.5%) of the title compound. The hydrochloride of this compound was obtained by converting the compound into hydrochloride in the usual manner, and then recrystallizing the salt from ethanol-ether.

EXAMPLE 15 Synthesis of 4-(4-(4-hydroxy-4-(2-pyridyl)-1-piperidinyl)butyl)-2,3,4,5-tetrahydro-1,4-benzoxazepine-3,5-dione

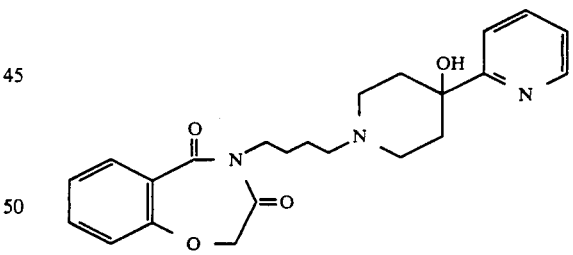

In 20 ml of dioxane was dissolved 326 mg of the compound obtained in Reference Example 8, 873 mg (3 equivalents) of 4-hydroxy-4-(2-pyridyl)piperidine.trifluoroacetate and 2.76 g (20 equivalents) of anhydrous potassium carbonate were added thereto, and the resulting mixture was refluxed for 3 days. The same procedures for reaction and treatment as used in Example 8 were repeated and the resulting residue was subjected to silica gel column chromatography (developing solution: methylene chloride-methanol (10:1)) to give 270 mg (yield: 66.0%) of the title compound. The hydrochloride of this compound was obtained by converting the compound into hydrochloride in the usual manner, and then recrystallizing the salt from ethanol-ether.

EXAMPLE 16 Synthesis of 4-(4-(4-(2-pyridyl)-1,2,3,6-tetrahydro-1-pyridyl)butyl)-2,3,4,5-tetrahydro-1,4-benzoxazepine-3,5-dione

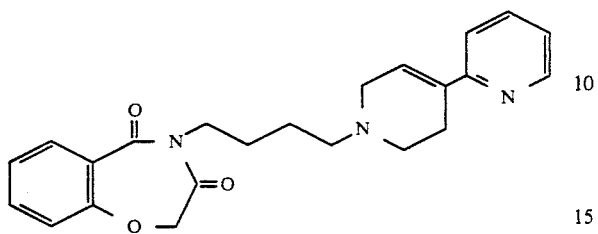

In 20 ml of dioxane was dissolved 260 mg of the compound obtained in Reference Example 8, 411 mg (1.9 equivalent) of 4-(2-pyridyl)-1,2,3,6-tetrahydropyridine.trifluoroacetate and 2.07 g (19 equivalents) of anhydrous potassium carbonate were added thereto, and the resulting mixture was refluxed for 23 hours. The dioxane was distilled off under a reduced pressure, ethyl acetate and conc. aqueous ammonia were added to the resulting residue to separate into solutions, the ethyl acetate phase was dried over anhydrous magnesium sulfate, and then the solvent was distilled off under a reduced pressure. The residue obtained was purified in the same manner as used in Example 8 to give 179 mg (yield: 57.0%) of the title compound. The hydrochloride of this compound was obtained by converting the compound into hydrochloride in the usual manner, and then recrystallizing the salt from ethanol-ether.

EXAMPLE 17 Synthesis of 4-(4-(4-phenyl)-1-piperidinyl)butyl-2,3,4,5-tetrahydro-1,4-benzothiazepine-3,5-dione

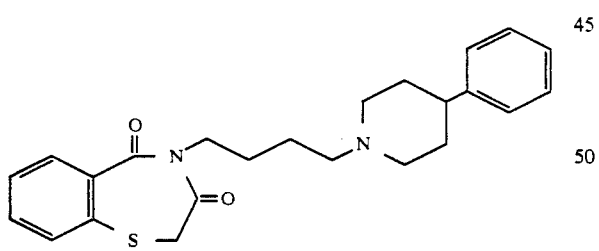

In 5 ml of dioxane was dissolved 27.0 mg of the compound prepared in Reference Example 9, then 41.5 mg (3 equivalents) of 4-phenylpiperidine was added thereto, and the resulting mixture was stirred at 110° C. for 3.5 hours with heating. Thereafter, the same procedures for reaction, treatment and purification as used in Example 1 were repeated to give 15.7 mg (yield: 46.3%) of the title compound. The maleate of this compound was obtained by converting the compound into maleate in the usual manner, and then recrystallizing the salt from methylene chloride-ether.

EXAMPLE 18 Synthesis of 4-(4-(4-phenyl)-1-piperidinyl)butyl-2,3,4,5-tetrahydro-1,4-benzodiazepine-3,5-dione

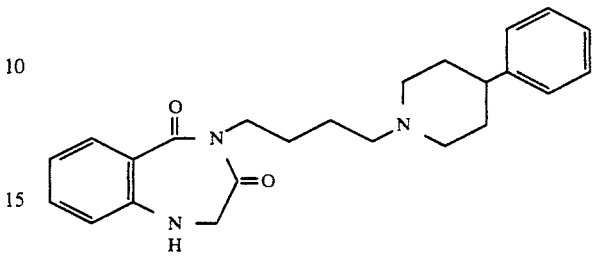

In 5ml of dioxane was dissolved 16.3 mg of the compound prepared in Reference Example 10, then 25.4 mg (3 equivalents) of 4-phenylpiperidine was added thereto, and the resulting mixture was stirred at 110° C. for 4 hours with heating. Thereafter, the same procedures for reaction, treatment and purification as used in Example 1 were repeated to give 16.9 mg (yield: 62.2%) of the title compound. The hydrochloride and fumarate of this compound were obtained by converting the compound into hydrochloride and fumarate in the usual manner, and then recrystallizing the salts from methylene chloride-ether.

EXAMPLE 19 Synthesis of 4-(4-(4-chlorophenyl)-1-piperidinyl)butyl-2,3,4,5-tetrahydro-1,4-benzothiazepine-3,5-dione

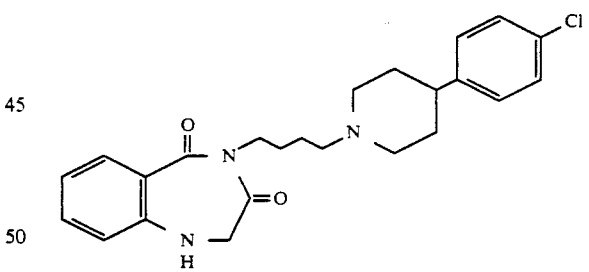

In 10 ml of dioxane was dissolved 33.0 mg of the compound prepared in Reference Example 10, then 31.1 mg (1.5 equivalent) of 4-(4-chlorophenyl)piperidine and 22.0 mg (1.5 equivalent) of potassium carbonate were added thereto, and the resulting mixture was stirred at 110° C. for 21 hours with heating. Thereafter, the same procedures for reaction, treatment and purification as used in Example 1 were repeated to give 29.3 mg (yield: 65.0%) of the title compound. The hydrochloride of this compound was obtained by converting the compound into hydrochloride in the usual manner, and then recrystallizing the salt from methylene chloride-ether.

EXAMPLE 20 Synthesis of 4-(4-(4-hydroxy-4-phenyl)-1-piperidinyl)butyl-2,3,4,5-tetrahydro-1,4-benzodiazepine-3,5-dione

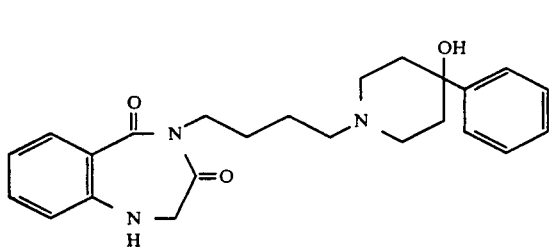

In 10 ml of dioxane was dissolved 44.8 mg of the compound prepared in Reference Example 10, then 76.5 mg (3 equivalents) of 4-hydroxy-4-phenylpiperidine was added thereto, and the resulting mixture was stirred at 100° C. for 4 hours with heating. Thereafter, the same procedures for reaction, treatment and purification as used in Example 1 were repeated to give 51.7 mg (yield: 88.2%) of the title compound. The hydrochloride of this compound was obtained by converting the compound into hydrochloride in the usual manner, and then recrystallizing the salt from methylene chloride-ether.

EXAMPLE 21 Synthesis of 1-methyl-4-(4-(4-phenyl)-1-piperidinyl)butyl-2,3,4,5-tetrahydro-1,4-benzodiazepine-3,5-dione

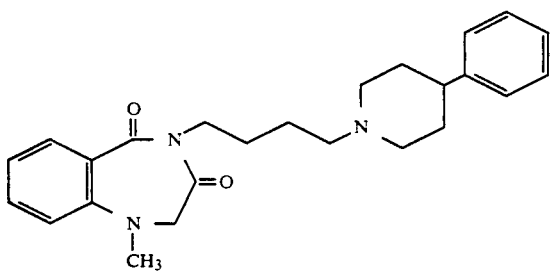

In 10 ml of dioxane was dissolved 56.9 mg of the compound prepared in Reference Example 11, then 62.0 mg (2.2 equivalents) of 4-phenylpiperidine was added thereto, and the resulting mixture was stirred at 110° C. for 12 hours with heating. Thereafter, the same procedures for reaction, treatment and purification as used in Example 1 were repeated to give 66.6 mg (yield: 93.9%) of the title compound. The fumarate of this compound was obtained by converting the compound into fumarate in the usual manner, and then recrystallizing the salt from methylene chloride-ether.

EXAMPLE 22: Synthesis of 2-(4-(4-phenyl)-1-piperidinyl)butyl-1,3,4,5-tetrahydro-2-benzazepine-1,3-dione

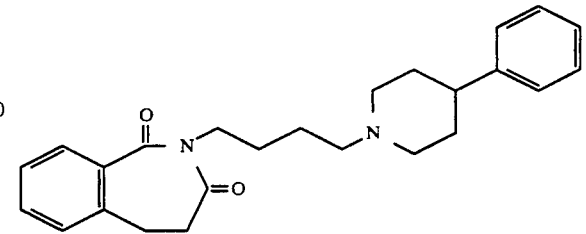

In 5 ml of dioxane was dissolved 19.7 mg of the compound prepared in Reference Example 12, then 30.7 mg (3 equivalents) of 4-phenylpiperidine was added thereto, and the resulting mixture was stirred at 110° C. for 4 hours with heating. Thereafter, the same procedures for reaction, treatment and purification as used in Example 1 were repeated to give 21.9 mg (yield: 88.3%) of the title compound. The hydrochloride of this compound was obtained by converting the compound into hydrochloride in the usual manner, and then recrystallizing the salt from methylene chloride-ether.

EXAMPLE 23 Synthesis of 2-(4-(4-(4-chlorophenyl)-1-piperidinyl)butyl)-1,3,4,5-tetrahydro-2-benzazepine-1,3-dione

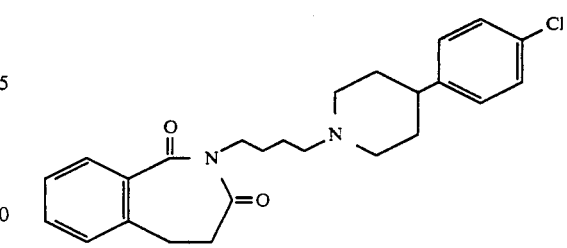

In 10 ml of dioxane was dissolved 20.0 mg of the compound prepared in Reference Example 12, then 18.9 mg (1.5 equivalents) of 4-(4-chlorophenyl)piperidine and 13.3 mg (1.5 equivalent) of potassium carbonate were added thereto, and the resulting mixture was stirred at 110° C. for 21 hours with heating. Thereafter, the same procedures for reaction, treatment and purification as used in Example 1 were repeated to give 19.9 mg (yield: 72.5%) of the title compound. The hydrochloride of this compound was obtained by converting the compound into hydrochloride in the usual manner, and then recrystallizing the salt from methylene chloride-ether.

EXAMPLE 24 Synthesis of 2-(4-(4-phenyl)-1-piperidinyl)butyl-1,3,4,5-tetrahydro-2-benzazepine-1,3-dione

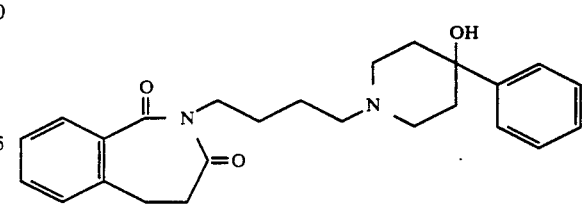

In 10ml of dioxane was dissolved 53.5 mg of the compound prepared in Reference Example 12, then 91.8 mg (3 equivalents) of 4-hydroxy-4-phenylpiperidine was added thereto, and the resulting mixture was stirred at 110° C. for 4 hours with heating. Thereafter, the same procedures for reaction, treatment and purification as used in Example 1 were repeated to give 68.6 mg (yield: 98.0%) of the title compound. The hydrochloride of this compound was obtained by converting the compound into hydrochloride in the usual manner, and then recrystallizing the salt from methylene chloride-ether.

EXAMPLE 25 Synthesis of
2-(4-(4-(4-chlorophenyl)-4-hydroxy)-1-piperidinyl)butyl-1,3,4,5-tetrahydro-2-benzazepine-1,3-dione

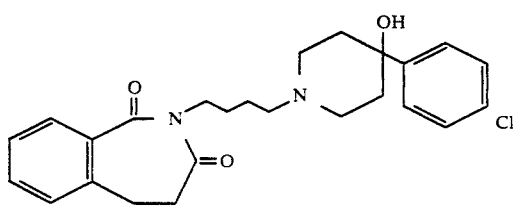

In 10 ml of dioxane was dissolved 39.0 mg of the compound prepared in Reference Example 12, then 79.8 mg (3 equivalents) of 4-(4-chlorophenyl)-4-hydroxypiperidine was added thereto, and the resulting mixture was stirred at 120° C. for 5 hours with heating. Thereafter, the same procedures for reaction, treatment and purification as used in Example 1 were repeated to give 52.0 mg (yield: 93.8%) of the title compound. The hydrochloride of this compound was obtained by converting the compound into hydrochloride in the usual manner, and then recrystallizing the salt from methylene chloride-ether.

EXAMPLE 26 Synthesis of
4-(5-(4-phenyl)-1-piperidinyl)pentyl-2,3,4,5-tetrahydro-1,4-benzoxazepin-5-one

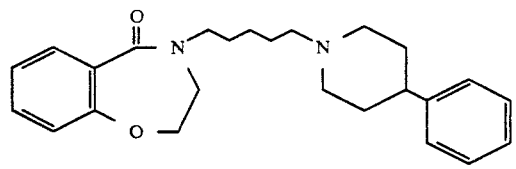

In 10 ml of dioxane was dissolved 80.0 mg of the compound prepared in Reference Example 1, then 95 mg (2.2 equivalents) of 4-phenylpiperidine was added thereto, and the resulting mixture was stirred at 100° C. for 6 hours with heating. Thereafter, the same procedures for reaction, treatment and purification as used in Example 1 were repeated to give 94.8 mg (yield: 93.4%) of the title compound. The hydrochloride of this compound was obtained by converting the compound into hydrochloride in the usual manner, and then recrystallizing the salt from methylene chloride-ether.

EXAMPLE 27 Synthesis of
4-(5-(4-(4-chlorochenyl)1-piperidinyl)pentyl)-2,3,4,5-tetrahydro-1,4-benzoxazepin-5-one

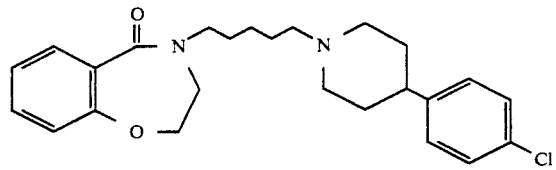

In 10 ml of dioxane was dissolved 64.5 mg of the compound prepared in Reference Example 1, then 116 mg (3 equivalents) of 4-(4-chlorophenyl)piperidine was added thereto, and the resulting mixture was stirred at 110° C. for 6 hours with heating. Thereafter, the same procedures for reaction, treatment and purification as used in Example 1 were repeated to give 86.3 mg (yield: 99.0%) of the title compound. The hydrochloride of this compound was obtained by converting the compound into hydrochloride in the usual manner, and then recrystallizing the salt from methylene chloride-ether.

EXAMPLE 28 Synthesis of
4-(5-(4-phenyl)-1-piperidinyl)pentyl-2,3,4,5-tetrahydro-1,4-benzoxazepin-3-one

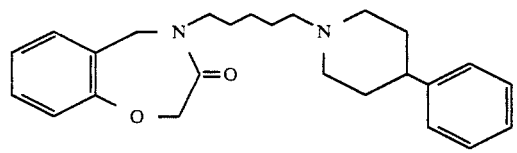

In 10 ml of dioxane was dissolved 65.0 mg of the compound prepared in Reference Example 2, then 96.0 mg (3 equivalents) of 4-phenylpiperidine was added thereto, and the resulting mixture was stirred at 110° C. for 8 hours with heating. Thereafter, the same procedures for reaction, treatment and purification as used in Example 1 were repeated to give 49.0 mg (yield: 60.0%) of the title compound. The hydrochloride of this compound was obtained by converting the compound into hydrochloride in the usual manner, and then recrystallizing the salt from methylene chloride-ether.

EXAMPLE 29 Synthesis of
4-(5-(4-(4-chlorophenyl)1-piperidinyl)pentyl-2,3,4,5-tetrahydro-1,4-benzoxazepin-3-one

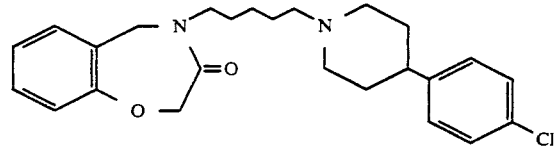

In 10 ml of dioxane was dissolved 65.2 mg of the compound prepared in Reference Example 2, then 123 mg (3 equivalents) of 4-(4-chlorophenyl)piperidine was added thereto, and the resulting mixture was stirred at 110° C. for 6 hours with heating. Thereafter, the same procedures for reaction, treatment and purification as used in Example 1 were repeated to give 46.7 mg (yield: 52.4%) of the title compound. The hydrochloride of this compound was obtained by converting the compound into hydrochloride in the usual manner, and then recrystallizing the salt from methylene chloride-ether.

EXAMPLE 30 Synthesis of 4-(5-(4-phenyl)-1-piperidinyl)pentyl-2,3,4,5-tetrahydro-1,4-benzoxazepine-3,5-dione

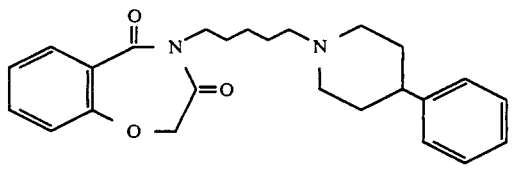

In 10 ml of dioxane was dissolved 40.0 mg of the compound prepared in Reference Example 13, then 62.0 mg (3 equivalents) of 4-phenylpiperidine was added thereto, and the resulting mixture was stirred at 100° C. for 3 hours with heating. Thereafter, the same procedures for reaction, treatment and purification as used in Example 1 were repeated to give 39.8 mg (yield: 79.2%) of the title compound. The hydrochloride of this compound was obtained by converting the compound into hydrochloride in the usual manner, and then recrystallizing the salt from methylene chloride-ether.

EXAMPLE 31 Synthesis of 4-(5-(4-(4-chlorophenyl)-1-piperidinyl)pentyl-2,3,4,5-tetrahydro-1,4-benzoxazepine-3,5-dione

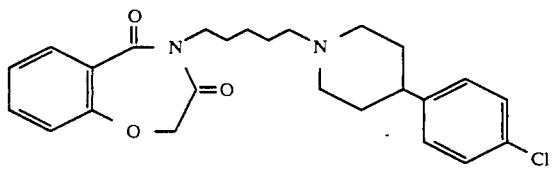

In 20 ml of dioxane was dissolved 100 mg of the compound prepared in Reference Example 13, then 173 mg (3 equivalents) of 4-(4-chlorophenyl)piperidine was added thereto, and the resulting mixture was stirred at 110° C. for 7 hours with heating. Thereafter, the same procedures for reaction, treatment and purification as used in Example 1 were repeated to give 123 mg (yield: 92.0%) of the title compound. The hydrochloride of this compound was obtained by converting the compound into hydrochloride in the usual manner, and then recrystallizing the salt from methylene chloride-ether.

EXAMPLE 32 Synthesis of 4-(5-(4-phenyl)-1-piperidinyl)pentyl-2,3,4,5-tetrahydro-1,4-benzothiazepine-3,5-dione

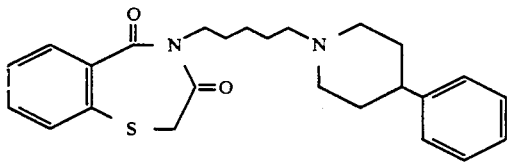

In 5 ml of dioxane was dissolved 30.5 mg of the compound prepared in Reference Example 3, then 29.0 mg (2.2 equivalents) of 4-phenylpiperidine was added thereto, and the resulting mixture was stirred at 110° C. for 24 hours with heating. Thereafter, the same procedures for reaction, treatment and purification as used in Example 1 were repeated to give 33.4 mg (yield: 88.0%) of the title compound. The maleate and fumarate of this compound was obtained by converting the compound into maleate and fumarate in the usual manner, and then fumarate was recrystallized from ether-hexane.

EXAMPLE 33 Synthesis of 4-(5-(4-(4-phenyl)-1-piperidinyl)pentyl)-2,3,4,5-tetrahydro-1,4-benzothiazepine-3,5-dione

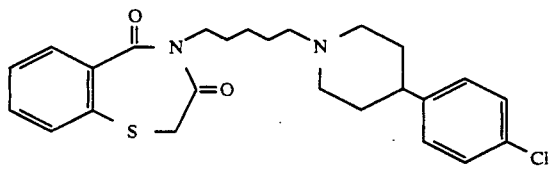

In 10 ml of dioxane was dissolved 44.0 mg of the compound prepared in Reference Example 3, then 57.7 mg (2.2 equivalents) of 4-(4-chlorophenyl)piperidine was added thereto, and the resulting mixture was stirred at 110° C. for 30 hours with heating. Thereafter, the same procedures for reaction, treatment and purification as used in Example 1 were repeated to give 37.5 mg (yield: 63.1%) of the title compound. The maleate of this compound was obtained by converting the compound into maleate in the usual manner.

EXAMPLE 34 Synthesis of 4-(5-(4-phenyl)-1-piperidinyl)pentyl-2,3,4,5-tetrahydro-1,4-benzodiazepine-3,5-dione

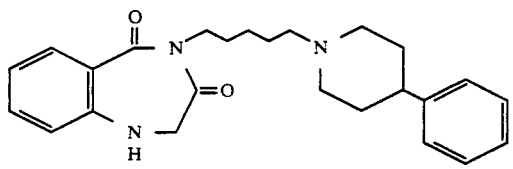

In 5 ml of dioxane was dissolved 57.8 mg of the compound prepared in Reference Example 4, then 86.0 mg (3 equivalents) of 4-phenylpiperidine was added thereto, and the resulting mixture was stirred at 100° C. for 8 hours with heating. Thereafter, the same procedures for reaction, treatment and purification as used in Example 1 were repeated to give 70.8 mg (yield: 98.3%) of the title compound. The fumarate of this compound was obtained by converting the compound into fumarate in the usual manner, and then recrystallizing the salt from acetone-ether.

EXAMPLE 35 Synthesis of 4-(5-(4-(4-chlorophenyl)-1-piperidinyl)pentyl)-2,3,4,5-tetrahydro-1,4-benzodiazepine-3,5-dione

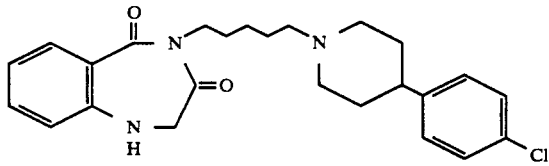

In 5 ml of dioxane was dissolved 40.9 mg of the compound prepared in Reference Example 4, then 61.5 mg (2.5 equivalents) of 4-(4-chlorophenyl)piperidine was added thereto, and the resulting mixture was stirred at 100° C. for 12 hours with heating. Thereafter, the same procedures for reaction, treatment and purification as used in Example 1 were repeated to give 49.9 mg (yield:

90.2%) of the title compound. The fumarate of this compound was obtained by converting the compound into fumarate in the usual manner, and then recrystallizing the salt from acetone-ether.

EXAMPLE 36 Synthesis of 2-(5-(4-phenyl)-1-piperidinyl)pentyl-1,3,4,5-tetrahydro-2-benzazepine-1,3-dione

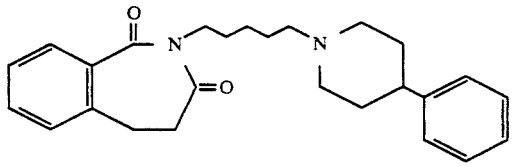

In 8 ml of dioxane was dissolved 44.0 mg of the compound prepared in Reference Example 5, then 48.2 mg (2.2 equivalents) of 4-phenylpiperidine was added thereto, and the resulting mixture was stirred at 110° C for 6 hours with heating. Thereafter, the same procedures for reaction, treatment and purification as used in Example 1 were repeated to give 46.6 mg (yield: 85.0%) of the title compound. The hydrochloride of this compound was obtained by converting the compound into hydrochloride in the usual manner, and then recrystallizing the salt from methylene chloride-ether.

EXAMPLE 37 Synthesis of 2-(5-(4-(4-chlorophenyl)-1-piperidinyl)pentyl)-1,3,4,5-tetrahydro-2-benzazepine-1,3-dione

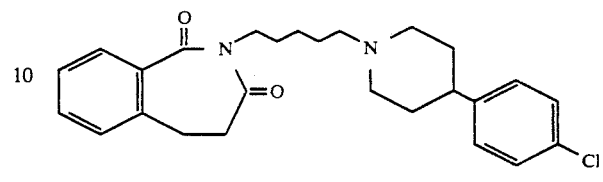

In 10 ml of dioxane was dissolved 61.2 mg of the compound prepared in Reference Example 5, then 111 mg (3 equivalents) of 4-(4-chlorophenyl)piperidine was added thereto, and the resulting mixture was stirred at 110° C. for 7 hours with heating. Thereafter, the same procedures for reaction, treatment and purification as used in Example 1 were repeated to give 66.7 mg (yield: 79.6%) of the title compound. The hydrochloride of this compound was obtained by converting the compound into hydrochloride in the usual manner, and then recrystallizing the salt from methylene chloride-ether.

The physical data of the compounds prepared in Examples 1 to 37 are summarized in Table II.

TABLE II

| Ex. No. | m.p. | IR (cm$^{-1}$) | | NMR (δppm) | Elemental Analysis | | | |
|---|---|---|---|---|---|---|---|---|
| 1 | 202–205° C. | 2920 | 2750 | 1.59–1.78(m, 6H), 1.82–1.86(m, 2H) | HCl salt ¼ H$_2$O | | | |
| | (HCl salt) | 1630 | 1600 | 2.02–2.09(m, 2H), 2.42–2.54(m, 3H) | | C | H | N |
| | | 1465 | 1450 | 3.05–3.09(m, 2H), 3.51(t, 2H, J=5.3Hz) | Calc. | 68.72 | 7.57 | 6.68 |
| | | 1410 | 1360 | 3.62–3.67(m, 2H), 4.38(t, 2H, J=5.3Hz) | Obsd. | 68.98 | 7.53 | 6.74 |
| | | 1280 | 1205 | 7.00(d, 1H, J=7.9Hz) | | | | |
| | | 1100 | 1040 | 7.16–7.32(m, 6H) | | | | |
| | | 800 | 755 | 7.40(ddd, 1H, J=1.3Hz&7.3Hz&7.9Hz) | | | | |
| | | | 695 | 7.80(dd, 1H, J=1.3Hz&7.9Hz) | | | | |
| 2 | 205–207° C. | 2920 | 2740 | 1.57–1.81(m, 8H), 1.96–2.06(m, 2H) | HCl salt ¾ H$_2$O | | | |
| | (HCl salt) | 1635 | 1600 | 2.38–2.50(m, 3H), 3.00–3.04(m, 2H) | | C | H | N |
| | | 1465 | 1410 | 3.46(t, 2H, J=5.3Hz) | Calc. | 62.26 | 6.86 | 6.05 |
| | | 1370 | 1310 | 3.58–3.63(m, 2H) | Obsd. | 62.12 | 6.56 | 6.02 |
| | | 1280 | 1205 | 4.34(t, 2H, J=5.3Hz) | | | | |
| | | 1105 | 1080 | 6.97(d, 1H, J=7.9Hz) | | | | |
| | | 1040 | 1005 | 7.09–7.40(m, 6H) | | | | |
| | | 820 | 800 | 7.77(dd, 1H, J=1.3Hz&7.9Hz) | | | | |
| | | 755 | 695 | | | | | |
| 3 | 192–194° C. | 3350 | 2930 | 1.50–1.82(m, 6H), 2.23–2.38(m, 2H) | HCl salt ¼ H$_2$O | | | |
| | (HCl salt) | 2820 | 1625 | 2.55–2.68(m, 4H) | | C | H | N |
| | | 1470 | 1420 | 3.51(t, 2H, J=5.3Hz) | Calc. | 66.19 | 7.29 | 6.43 |
| | | 1380 | 1305 | 3.66(t, 2H, J=6.6Hz) | Obsd. | 66.08 | 7.42 | 6.42 |
| | | 1280 | 1210 | 4.38(t, 2H, J=5.3Hz)7.00(d, 1H, J=8.6Hz) | | | | |
| | | 1120 | 1040 | 7.16(dd, 1H, J=7.3Hz&7.9Hz) | | | | |
| | | 980 | 800 | 7.30–7.44(m, 4H) | | | | |
| | | 760 | 730 | 7.52(d, 2H, J=7.3Hz) | | | | |
| | | | 695 | 7.79(dd, 1H, J=1.3Hz&7.3Hz) | | | | |
| 4 | 189–190° C. | 2920 | 2750 | 1.44–1.59(m, 4H), 1.71–1.78(m, 4H) | HCl salt ¼ H$_2$O | | | |
| | (HCl salt) | 1660 | 1630 | 1.93–2.02(m, 2H), 2.31–2.45(m, 3H) | | C | H | N |
| | | 1570 | 1485 | 2.93–2.97(m, 2H), 3.48–3.53(m, 2H) | Calc. | 68.72 | 7.57 | 6.68 |
| | | 1470 | 1430 | 4.43(s, 2H), 4.62(s, 2H) | Obsd. | 68.71 | 7.44 | 6.71 |
| | | 1340 | 1300 | 6.95–7.00(m, 2H) | | | | |
| | | 1220 | 1185 | 7.09–7.25(m, 7H) | | | | |
| | | 1115 | 1050 | | | | | |
| | | 1015 | 750 | | | | | |
| | | 690 | | | | | | |
| 5 | 167–169° C. | 2920 | 2750 | 1.48–1.64(m, 4H), 1.72–1.80(m, 4H) | HCl salt | | | |
| | (HCl salt) | 1660 | 1575 | 1.97–2.04(m, 2H), 2.36–2.49(m, 3H) | | C | H | N |
| | | 1485 | 1450 | 2.97–3.02(m, 2H), 3.52–3.57(m, 2H) | Calc. | 64.14 | 6.73 | 6.23 |
| | | 1340 | 1300 | 4.47(s, 2H) | Obsd. | 64.00 | 7.02 | 6.15 |
| | | 1220 | 1190 | 4.67(s, 2H) | | | | |
| | | 1120 | 1090 | 6.99–7.25(m, 8H) | | | | |
| | | 1050 | 1010 | | | | | |
| | | 820 | 755 | | | | | |
| | | 690 | | | | | | |
| 6 | 176–179° C. | 3350 | 2920 | 1.56–1.81(m, 6H), 2.32–2.34(m, 2H) | HCl salt ¼ H$_2$O | | | |

TABLE II-continued

| Ex. No. | m.p. | IR (cm⁻¹) | | NMR (δppm) | Elemental Analysis | | | |
|---|---|---|---|---|---|---|---|---|
| | (HCl salt) | 2810 | 1650 | 2.57-2.65(m, 4H), 2.90-2.94(m, 2H) | | C | H | N |
| | | 1570 | 1485 | 3.59(t, 2H), J=6.6Hz) | Calc. | 65.51 | 7.33 | 6.37 |
| | | 1440 | 1345 | 4.51(s, 2H), 4.70(s, 2H) | | 65.80 | 7.38 | 6.43 |
| | | 1300 | 1220 | 7.02-7.07(m, 2H) | | | | |
| | | 1185 | 1125 | 7.18-7.53(m, 7H) | | | | |
| | | 1040 | 1020 | | | | | |
| | | 755 | 695 | | | | | |
| 7 | 182-184° C. | 3350 | 2920 | 1.48-1.74(m, 6H) | HCl salt | | | |
| | (HCl salt) | 2800 | 1640 | 2.09-2.20(m, 2H) | | C | H | N |
| | | 1485 | 1460 | 2.39-2.50(m, 4H) | Calc. | 61.93 | 6.50 | 6.02 |
| | | 1430 | 1360 | 2.78-2.82(m, 2H) | Obsd. | 61.66 | 6.45 | 5.98 |
| | | 1300 | 1220 | 3.55-3.60(m, 2H) | | | | |
| | | 1190 | 1125 | 4.50(s, 2H), 4.70(s, 2H) | | | | |
| | | 1090 | 1040 | 7.02-7.46(m, 8H) | | | | |
| | | 1010 | 910 | | | | | |
| | | 820 | 755 | | | | | |
| | | 730 | 695 | | | | | |
| 8 | 174-176° C. | 2940 | 2800 | 1.52-1.83(m, 8H), | HCl salt ¾ H₂O | | | |
| | (HCl salt) | 2770 | 1705 | 2.04(m, 2H) | | C | H | N |
| | | 1650 | 1600 | 2.40(t, 2H, J=7.3Hz) | Calc. | 65.15 | 6.94 | 6.33 |
| | | 1490 | 1460 | 2.48(m, 1H), 3.04(d, 2H, J=11.2Hz) | Obsd. | 65.00 | 6.56 | 6.25 |
| | | 1290 | 1210 | 4.02(t, 2H, J=7.9Hz), 4.75(s, 2H) | | | | |
| | | 1110 | 1060 | 7.08(dd, 1H, J=1.3Hz&7.9Hz) | | | | |
| | | 1040 | 760 | 7.15-7.31(m, 6H) | | | | |
| | | 700 | | 7.51(m, 1H) | | | | |
| | | | | 8.16(dd, 1H, J=1.3Hz&7.9Hz) | | | | |
| 9 | 202-204° C. | 2910 | 2750 | 1.55-1.83(m, 8H), 1.98-2.08(m, 2H) | HCl salt | | | |
| | (HCl salt) | 1700 | 1645 | 2.38-2.51(m, 3H) | | C | H | N |
| | | 1600 | 1480 | 3.02-3.07(m, 2H), 4.01(t, 2H, J=7.3Hz) | Calc. | 62.20 | 6.09 | 6.05 |
| | | 1440 | 1360 | 4.75(s, 2H), 7.08-7.30(m, 6H) | Obsd. | 62.51 | 6.36 | 5.96 |
| | | 1330 | 1290 | 7.51(ddd, 1H, J=1.3Hz&7.9Hz&8.6Hz) | | | | |
| | | 1210 | 1120 | 8.17(dd, 1H, J=1.3Hz&7.9Hz) | | | | |
| | | 1080 | 1005 | | | | | |
| | | 815 | 780 | | | | | |
| | | 760 | 690 | | | | | |
| 10 | 151-153° C. | 3350 | 2930 | 1.47-1.79(m, 6H) | HCl salt ¼ H₂O | | | |
| | (HCl salt) | 2800 | 1700 | 2.14-2.25(m, 2H), 2.41-2.51(m, 4H) | | C | H | N |
| | | 1640 | 1600 | 2.64-2.88(m, 2H) | Calc. | 64.13 | 6.62 | 6.23 |
| | | 1480 | 1445 | 3.99-4.05(m, 2H) | Obsd. | 64.32 | 6.77 | 6.26 |
| | | 1360 | 1335 | 4.76(s, 2H) | | | | |
| | | 1290 | 1215 | 7.10(d, 1H, J=7.9Hz) | | | | |
| | | 1040 | 955 | 7.21-7.55(m, 7H) | | | | |
| | | 815 | 755 | 8.17(dd, 1H, J=1.7Hz&7.9Hz) | | | | |
| | | 695 | | | | | | |
| 11 | 186-188° C. | 3300 | 2900 | 1.44-1.75(m, 6H), | HCl salt | | | |
| | (HCl salt) | 2750 | 1695 | 2.05-2.20(m, 2H) | | C | H | N |
| | | 1640 | 1600 | 2.35-2.55(m, 4H) | Calc. | 60.13 | 5.89 | 5.84 |
| | | 1475 | 1445 | 2.78-2.90(m, 2H), 3.98-4.03(m, 2H) | Obsd. | 59.98 | 5.82 | 5.79 |
| | | 1360 | 1330 | 4.76(s, 2H) | | | | |
| | | 1285 | 1205 | 7.08(d, 1H, J=7.9Hz) | | | | |
| | | 1115 | 1080 | 7.21-7.54(m, 6H) | | | | |
| | | 1035 | 820 | 8.15(dd, 1H, J=1.3Hz&7.9Hz) | | | | |
| | | 760 | | | | | | |
| 12 | 141-145° C. | 2550 | 1710 | 1.60-1.78(m, 4H) | Mass | | | |
| | (HCl salt) | 1640 | 1480 | 2.50(t, 2H), J=7.9Hz), 2.57(m, 2H) | HiMs | (free base) | | |
| | | 1450 | 1300 | 2.70(t, 2H, J=5.3Hz), 3.14(m, 2H) | Calc. | 390.1942 | | |
| | | 1220 | 1120 | 4.03(t, 2H, J=7.9Hz), 4.75(s, 2H) | Obsd. | 390.1943 | | |
| | | | | 6.05(m, 1H), 7.09(dd, 1H, J=1.3Hz&7.9Hz) | | | | |
| | | | | 7.20-7.40(m, 6H) | | | | |
| | | | | 7.51(m, 1H) | | | | |
| | | | | 8.16(dd, 1H, J=1.3Hz&7.9Hz) | | | | |
| 13 | 155-158° C. | 2880 | 2750 | 1.49-1.70(m, 4H) | HCl salt ¼ H₂O | | | |
| | (HCl salt) | 1700 | 1640 | 2.41-2.45(m, 4H), 2.61-2.65(m, 2H) | | C | H | N |
| | | 1600 | 1480 | 3.06-3.08(m, 2H), 3.92-3.98(m, 2H) | Calc. | 60.30 | 5.89 | 5.84 |
| | | 1440 | 1335 | 4.68(s, 2H), 5.96-5.98(m, 2H) | Obsd. | 60.03 | 5.66 | 5.87 |
| | | 1290 | 1215 | 7.02(d, 1H, J=7.9Hz) | | | | |
| | | 1120 | 1090 | 7.14-7.47(m, 6H) | | | | |
| | | 1040 | 820 | 8.09(dd, 1H, J=1.3Hz&8.4Hz) | | | | |
| | | 760 | | | | | | |
| 14 | 167-170° C. | 2940 | 1705 | 1.57-2.12(m, 10H), | Mass | | | |
| | (HCl salt) | 1650 | 1600 | 2.42(t, 2H, J=7.3Hz), 2.71(m, 1H) | HiMs | (free base) | | |
| | | 1480 | 1460 | 3.06(d, 2H, J=11.9Hz), 4.02(t, 2H, J=7.9Hz) | Calc. | 393.2051 | | |
| | | 1440 | 1300 | 4.76(s, 2H), 7.09(dd, 1H, J=1.3Hz, &7.9Hz) | Obsd. | 393.2057 | | |
| | | 1220 | 1130 | 7.12-7.23(m, 3H), 7.51(m, 1H) | | | | |
| | | 1040 | 760 | 7.61(m, 1H), 8.16(dd, 1H, J=1.3Hz&7.9Hz) | | | | |
| | | | | 8.51(dd, 1H, J=1.3Hz&4.0Hz) | | | | |
| 15 | 188-190° C. | 3300 | 2950 | 1.56-1.77(m, 6H), 1.94(br, s, 1H) | Mass | | | |
| | (HCl salt) | 2820 | 1705 | 2.11(dt, 2H, J=4.6Hz&12.5Hz) | HiMs | (free base) | | |
| | | 1650 | 1600 | 2.47-2.57(m, 4H), 2.88(m, 2H) | Calc. | 409.2000 | | |

TABLE II-continued

| Ex. No. | m.p. | IR (cm$^{-1}$) | | NMR (δppm) | Elemental Analysis | | | |
|---|---|---|---|---|---|---|---|---|
| | | 1490 | 1460 | 4.02(t, 2H, J=7.9Hz), 4.76(s, 2H) | Obsd. 409.2004 | | | |
| | | 1440 | 1300 | 7.09(dd, 1H, J=1.3Hz&7.9Hz) | | | | |
| | | 1220 | 1130 | 7.18-7.24(m, 2H), 7.40(d, 1H, J=7.9Hz) | | | | |
| | | 1050 | 790 | 7.51(m, 1H), 7.71(m, 1H) | | | | |
| | | | | 8.16(dd, 1H, J=1.3Hz&7.9Hz) | | | | |
| | | | | 8.51(d, 1H, J=4.6Hz) | | | | |
| 16 | 172-175° C. | 2920 | 2800 | 1.55-1.75(m, 4H), 2.52(t, 2H, J=7.9Hz) | Mass | | | |
| | (HCl salt) | 1700 | 1650 | 2.65-2.75(m, 4H), 3.22(m, 2H) | HiMs | (free base) | | |
| | | 1600 | 1580 | 4.03(t, 2H, J=7.3Hz), 4.75(s, 2H) | Calc. | 391.1893 | | |
| | | 1480 | 1460 | 6.62(s, 1H), 7.07-7.14(m, 2H) | Obsd. | 391.1881 | | |
| | | 1450 | 1430 | 7.23(m, 1H), 7.36(d, 1H, J=8.6Hz) | | | | |
| | | 1370 | 1290 | 7.51(m, 1H), 7.62(m, 1H) | | | | |
| | | 1220 | 1120 | 8.16(dd, 1H, J=1.3Hz&7.9Hz) | | | | |
| | | 1040 | 760 | 8.55(d, 1H, J=4.0Hz) | | | | |
| 17 | 103-105° C. | 2920 | 2750 | 1.51-1.83(m, 8H) | Maleate | | | |
| | (Maleate) | 1695 | 1635 | 1.98-2.07(m, 2H) | | C | H | N |
| | | 1580 | 1440 | 2.37-2.50(m, 3H), 3.01-3.06(m, 2H) | Calc. | 64.10 | 6.15 | 5.34 |
| | | 1430 | 1350 | 3.68(s, 2H), 4.03(t, 2H, J=7.2Hz) | Obsd. | 63.76 | 6.35 | 5.22 |
| | | 1320 | 1265 | 7.16-7.49(m, 8H) | | | | |
| | | 1110 | 1085 | 8.17-8.21(m, 1H) | | | | |
| | | 780 | 740 | | | | | |
| | | 695 | | | | | | |
| 18 | 153-155° C. | 3250 | 2920 | 1.40-1.63(m, 4H), 1.66-1.75(m, 4H) | HCl salt H$_2$O | | | |
| | (Fumarate) | 2850 | 1685 | 1.89-1.98(m, 3H), 2.92-2.96(m, 2H) | | C | H | N |
| | | 1630 | 1600 | 3.83(d, 2H, J=4.6Hz), 3.83-3.89(m, 2H) | Calc. | 64.63 | 7.23 | 9.42 |
| | | 1485 | 1425 | 4.77(t, 1H) | Obsd. | 64.92 | 7.09 | 9.36 |
| | | 1360 | 1315 | 6.70(d, 1H, J=7.9Hz) | | | | |
| | | 1285 | 1150 | 6.87(dd, 1H, J=7.3Hz&7.9Hz) | | | | |
| | | 1120 | 1010 | 7.08-7.30(m, 6H) | | | | |
| | | 970 | 780 | 8.18(dd, 1H, J=1.3Hz&7.9Hz) | | | | |
| | | 740 | 690 | | | | | |
| 19 | Undeterminable | 3300 | 2920 | 1.49-1.81(m, 8H), 1.95-2.04(m, 2H) | HCl salt H$_2$O | | | |
| | because of | 2750 | 1690 | 2.31-2.49(m, 3H), 2.98-3.03(m, 2H) | | C | H | N |
| | hygroscopicity | 1635 | 1600 | 3.90(d, 2H, J=4.6Hz), 3.93(t, 2H, J=7.3Hz) | Calc. | 60.00 | 6.50 | 8.75 |
| | (HCl salt) | 1485 | 1425 | 4.91(t, 1H, J=4.6Hz) | Obsd. | 59.76 | 6.70 | 8.62 |
| | | 1360 | 1315 | 6.78(d, 1H, J=7.9Hz) | | | | |
| | | 1290 | 1120 | 6.94(dd, 1H, J=7.2Hz&7.9Hz) | | | | |
| | | 1085 | 1005 | 7.12-7.37(m, 5H) | | | | |
| | | 970 | 820 | 8.25(dd, 1H, J=1.3Hz&7.9Hz) | | | | |
| | | 780 | 745 | | | | | |
| | | 695 | | | | | | |
| 20 | 203-205° C. | 3300 | 2930 | 1.41-1.76(m, 6H), 2.10-2.22(m, 2H) | HCl salt ½ H$_2$O | | | |
| | (HCl salt) | 2800 | 1685 | 2.38-2.46(m, 4H), 2.78-2.82(m, 2H) | | C | H | N |
| | | 1625 | 1600 | 3.91(d, 2H, J=4.6Hz), 3.49(t, 2H, J=6.6Hz) | Calc. | 63.63 | 6.90 | 9.28 |
| | | 1480 | 1420 | 4.75(t, 1H, J=4.6Hz) | Obsd. | 63.21 | 6.79 | 9.18 |
| | | 1360 | 1315 | 6.78(d, 1H, J=7.9Hz) | | | | |
| | | 1290 | 1120 | 6.95(dd, 1H, J=7.3Hz&8.6Hz), | | | | |
| | | 1035 | 970 | 7.23-7.38(m, 4H) | | | | |
| | | 775 | 745 | 7.51(d, 2H, J=7.2Hz) | | | | |
| | | 690 | | 8.26(dd, 1H, J=1.3Hz&8.6Hz), | | | | |
| 21 | 153-155° C. | 2910 | 2750 | 1.51-1.81(m, 6H) | Fumarate ½ H$_2$O | | | |
| | (Fumarate) | 1690 | 1630 | 1.95-2.07(m, 2H), 2.37(t, 2H, J=7.2Hz) | | C | H | N |
| | | 1595 | 1490 | 2.37-2.53(m, 1H), 2.98-3.02 (m, 2H) | Calc. | 65.64 | 6.84 | 7.92 |
| | | 1430 | 1360 | 3.22(s, 3H), 3.85(s, 2H) | Obsd. | 65.49 | 6.88 | 7.94 |
| | | 1325 | 1260 | 3.89-3.94(m, 2H) | | | | |
| | | 1240 | 1190 | 6.91-6.98(m, 2H) | | | | |
| | | 1100 | 1070 | 7.18-7.46(m, 6H) | | | | |
| | | 995 | 775 | 8.32(d, 1H, J=7.9Hz) | | | | |
| | | 745 | 695 | | | | | |
| 22 | 175-177° C. | 2920 | 2730 | 1.47-1.78(m, 8H) | HCl salt ½ H$_2$O | | | |
| | (HCl salt) | 1690 | 1635 | 1.92-2.02(m, 2H), 2.32-2.43(m, 3H) | | C | H | N |
| | | 1595 | 1485 | 2.92(s, 4H), 2.92-3.01(m, 2H) | Calc. | 68.87 | 7.40 | 6.43 |
| | | 1440 | 1305 | 3.93-3.98(m, 2H) | Obsd. | 69.13 | 7.23 | 6.43 |
| | | 1265 | 1180 | 7.08-7.37(m, 8H) | | | | |
| | | 1100 | 745 | 7.89(dd, 1H, J=1.3Hz&7.9Hz) | | | | |
| | | 690 | | | | | | |
| 23 | 180-182° C. | 2920 | 2750 | 1.55-1.81(m, 8H) | HCl salt | | | |
| | (HCl salt) | 1690 | 1640 | 1.99-2.08(m, 2H), 2.39-2.50(m, 3H) | | C | H | N |
| | | 1595 | 1490 | 2.99-3.07(m, 6H) | Calc. | 65.07 | 6.55 | 6.07 |
| | | 1440 | 1370 | 3.99-4.05(m, 2H) | Obsd. | 65.01 | 6.62 | 6.14 |
| | | 1335 | 1310 | 7.13-7.47(m, 7H) | | | | |
| | | 1270 | 1180 | 7.96(dd, 1H, J=1.3Hz&7.9Hz) | | | | |
| | | 1100 | 1005 | | | | | |
| | | 885 | 820 | | | | | |
| | | 750 | 710 | | | | | |
| 24 | 201-202° C. | 3350 | 2930 | 1.52-1.79(m, 6H) | HCl salt ¼ H$_2$O | | | |
| | (HCl salt) | 2800 | 1690 | 2.14-2.25(m, 2H), 2.41-2.51(m, 4H) | | C | H | N |
| | | 1640 | 1600 | 2.83-2.88(m, 2H), 3.00(s, 4H) | Calc. | 67.10 | 7.10 | 6.26 |
| | | 1490 | 1440 | 4.00-4.05(m, 2H) | Obsd. | 67.22 | 7.07 | 6.27 |

TABLE II-continued

| Ex. No. | m.p. | IR (cm$^{-1}$) | | NMR (δppm) | Elemental Analysis | | | |
|---|---|---|---|---|---|---|---|---|
| | | 1380 | 1300 | 7.17(d, 1H, J=7.3Hz) | | | | |
| | | 1265 | 1180 | 7.25-7.54(m, 7H) | | | | |
| | | 1105 | 1040 | 7.96(d, 1H, J=7.9Hz) | | | | |
| | | 960 | 790 | | | | | |
| | | 755 | 695 | | | | | |
| 25 | 186-188° C. | 3400 | 2920 | 1.49-1.75(m, 6H) | HCl salt | | | |
| | (HCl salt) | 2800 | 1690 | 2.09-2.20(m, 2H), 2.40-2.48(m, 4H) | | C | H | N |
| | | 1640 | 1600 | 2.84-2.96(m, 2H), 2.99(s, 4H) | Calc. | 62.89 | 6.33 | 5.87 |
| | | 1480 | 1440 | 4.03(t, 2H, J=7.3Hz) | Obsd. | 62.39 | 6.25 | 5.82 |
| | | 1340 | 1315 | 7.16(d, 1H, J=7.3Hz) | | | | |
| | | 1270 | 1185 | 7.29-7.46(m, 6H) | | | | |
| | | 1110 | 1040 | 7.96(d, 1H, J=7.9Hz) | | | | |
| | | 1010 | 960 | | | | | |
| | | 820 | 790 | | | | | |
| | | 750 | | | | | | |
| 26 | 178-180° C. | 3300 | 2920 | 1.39-1.72(m, 6H), 1.83-1.90(m, 4H) | HCl salt ½ H$_2$O | | | |
| | (HCl salt) | 2860 | 2750 | 2.06-2.15(m, 2H), 2.39-2.55(m, 3H) | | C | H | N |
| | | 1630 | 1600 | 3.07-3.15(m, 2H) | Calc. | 68.55 | 7.82 | 6.40 |
| | | 1460 | 1420 | 3.50(t, 2H, J=5.3Hz) | Obsd. | 69.00 | 7.65 | 6.41 |
| | | 1370 | 1315 | 3.60-3.65(m, 2H), 4.38(t, 2H, J=5.3Hz) | | | | |
| | | 1280 | 1210 | 7.00(d, 1H, J=8.7Hz) | | | | |
| | | 1105 | 1040 | 7.12-7.43(m, 7H), | | | | |
| | | 980 | 800 | 7.80(dd, 1H, J=2.0Hz&7.9Hz) | | | | |
| | | 755 | 695 | | | | | |
| 27 | 180-181° C. | 2900 | 2740 | 1.33-1.52(m, 2H), 1.53-1.88(m, 8H) | HCl salt | | | |
| | (HCl salt) | 1635 | 1600 | 2.02-2.10(m, 2H), 2.36-2.54(m, 3H) | | C | H | N |
| | | 1460 | 1410 | 3.06-3.10(m, 2H) | Calc. | 64.79 | 6.96 | 6.04 |
| | | 1360 | 1310 | 3.50(t, 2H, J=5.3Hz), 3.62(t, 2H, J=7.2Hz) | Obsd. | 64.64 | 6.93 | 6.03 |
| | | 1280 | 1205 | 4.38(t, 2H, J=5.3Hz), 7.00(d, 1H, J=7.9Hz) | | | | |
| | | 1085 | 1040 | 7.13-7.27(m, 5H), | | | | |
| | | 820 | 755 | 7.40(dt, 1H, J=1.3Hz&7.9Hz) | | | | |
| | | 690 | | 7.81(dd, 1H, J=1.3Hz&7.9Hz) | | | | |
| 28 | 161-163° C. | 2920 | 2730 | 1.26-1.40(m, 2H), 1.49-1.70(m, 4H) | HCl salt ½ H$_2$O | | | |
| | (HCl salt) | 1660 | 1630 | 1.78-1.89(m, 4H), 2.00-2.10(m, 2H) | | C | H | N |
| | | 1485 | 1450 | 2.33-2.39(m, 2H) | Calc. | 69.27 | 7.79 | 6.46 |
| | | 1340 | 1300 | 2.47-2.53(m, 1H) | Obsd. | 69.30 | 7.61 | 6.49 |
| | | 1220 | 1185 | 3.02-3.10(m, 2H) | | | | |
| | | 1105 | 1050 | 3.55(t, 2H, J=7.3Hz), 4.49(s, 2H) | | | | |
| | | 1020 | 750 | 4.69(s, 2H), 7.03-7.32 (m, 9H) | | | | |
| | | 695 | | | | | | |
| 29 | 144-148° C. | 2900 | 2850 | 1.25-1.36(m, 2H), 1.49-1.69(m, 4H) | HCl salt ½ H$_2$O | | | |
| | (HCl salt) | 2750 | 1660 | 1.70-1.82(m, 4H), 1.97-2.09(m, 2H) | | C | H | N |
| | | 1575 | 1480 | 2.32-2.37(m, 2H) | Calc. | 63.56 | 7.04 | 5.93 |
| | | 1440 | 1340 | 2.41-2.51(m, 1H), 3.03-3.07(m, 2H) | Obsd. | 63.38 | 6.86 | 5.91 |
| | | 1300 | 1215 | 3.52-3.58(m, 2H) | | | | |
| | | 1185 | 1080 | 4.49(s, 2H), 4.69(s, 2H) | | | | |
| | | 1045 | 1020 | 7.03-7.32(m, 8H), | | | | |
| | | 815 | 745 | | | | | |
| | | 690 | | | | | | |
| 30 | 176-178° C. | 2920 | 2750 | 1.33-1.72(m, 6H) | HCl salt ½ H$_2$O | | | |
| | (HCl salt) | 1700 | 1645 | 1.74-1.85(m, 4H), 1.98-2.06(m, 2H) | | C | H | N |
| | | 1600 | 1480 | 2.35-2.40(m, 2H), 2.45-2.51(m, 1H) | Calc. | 67.10 | 7.10 | 6.26 |
| | | 1445 | 1370 | 3.03-3.07(m, 2H), 3.96-4.01(m, 2H) | Obsd. | 67.16 | 7.09 | 6.28 |
| | | 1335 | 1290 | 4.76(s, 2H) | | | | |
| | | 1215 | 1115 | 7.09(d, 1H, J=7.9Hz) | | | | |
| | | 1060 | 1040 | 7.16-7.33(m, 6H) | | | | |
| | | 985 | 815 | 7.51(dt, 1H, J=1.3Hz&7.9Hz) | | | | |
| | | 755 | 695 | 8.17(dd, 1H, J=1.3Hz&7.9Hz) | | | | |
| 31 | 166-168° C. | 2910 | 2740 | 1.35-1.44(m, 2H) | HCl salt | | | |
| | (HCl salt) | 1700 | 1645 | 1.48-1.83(m, 8H) | | C | H | N |
| | | 1600 | 1475 | 1.96-2.05(m, 2H), 2.33-2.39(m, 2H) | Calc. | 62.89 | 6.33 | 5.87 |
| | | 1440 | 1360 | 2.42-2.52(m, 1H), 3.02-3.06(m, 2H) | Obsd. | 63.02 | 6.32 | 5.86 |
| | | 1325 | 1290 | 3.95-4.01(m, 2H), 4.76(s, 2H) | | | | |
| | | 1210 | 1115 | 7.08-7.27(m, 6H), | | | | |
| | | 1085 | 1035 | 7.51(dt, 1H, J=1.3Hz&7.9Hz) | | | | |
| | | 815 | 760 | 8.16(dt, 1H, J=1.3Hz&7.9Hz) | | | | |
| | | 690 | | | | | | |
| 32 | 124-128° C. | 2930 | 2750 | 1.31-1.50(m, 2H) | Fumarate ½ H$_2$O | | | |
| | (Fumarate) | 1695 | 1640 | 1.51-1.84(m, 8H), 1.94-2.07(m, 2H) | | C | H | N |
| | | 1580 | 1490 | 2.35(t, 2H), J=7.9Hz), 2.45-2.52(m, 1H) | Calc. | 63.60 | 6.44 | 5.12 |
| | | 1430 | 1350 | 3.02-3.06(m, 2H) | Obsd. | 63.73 | 6.41 | 5.11 |
| | | 1320 | 1255 | 3.68(s, 2H), 4.00(t, 2H, J=7.9Hz) | | | | |
| | | 1230 | 1085 | 7.16-7.47(m, 8H) | | | | |
| | | 985 | 780 | 8.17-8.21(m, 1H). | | | | |
| | | 740 | 695 | | | | | |
| 33 | Oily product | 2920 | 2750 | 1.33-1.47(m, 2H) | Maleate | | | |
| | (Maleate) | 1690 | 1630 | 1.50-1.85(m, 8H), 1.91-2.04(m, 2H) | | C | H | N |
| | | 1580 | 1490 | 2.35(t, 2H, J=7.3Hz) | Calc. | 60.77 | 5.80 | 4.89 |
| | | 1460 | 1430 | 2.39-2.52(m, 1H), 3.01-3.05(m, 2H) | Obsd. | 60.26 | 5.88 | 4.78 |

TABLE II-continued

| Ex. No. | m.p. | IR (cm$^{-1}$) | | NMR (δppm) | Elemental Analysis | | | |
|---|---|---|---|---|---|---|---|---|
| | | 1320 | 1255 | 3.68(s, 2H), 3.97-4.02(m, 2H) | | | | |
| | | 1230 | 1085 | 7.13-7.49(m, 7H) | | | | |
| | | 1010 | 985 | 8.19(dd, 1H, J=1.9Hz&7.9Hz) | | | | |
| | | 820 | 780 | | | | | |
| | | 740 | 685 | | | | | |
| 34 | 183-184° C. | 3250 | 2900 | 1.33-1.39(m, 2H), 1.52-1.84(m, 8H) | Fumarate ¼ H$_2$O | | | |
| | (Fumarate) | 2750 | 1685 | 1.98-2.07(m, 2H), 2.33-2.38(m, 2H) | | C | H | N |
| | | 1630 | 1600 | 2.45-2.48(m, 1H), 3.02-3.07(m, 2H) | Calc. | 65.64 | 6.84 | 7.92 |
| | | 1485 | 1425 | 3.91(d, 2H, J=4/6Hz), 3.90-3.93(m, 2H) | Obsd. | 65.24 | 6.63 | 7.72 |
| | | 1350 | 1310 | 4.71(t, 1H, J=4.6Hz), 6.77(d, 1H, J=7.9Hz) | | | | |
| | | 1290 | 1230 | 6.95(t, 1H, J=7.9Hz), | | | | |
| | | 1150 | 1110 | 7.19-7.37(m, 6H) | | | | |
| | | 970 | 745 | 8.26(dd, 1H, J=1.3Hz&7.9Hz) | | | | |
| | | 690 | | | | | | |
| 35 | 171-173° C. | 3250 | 2900 | 1.25-1.39(m, 2H), 1.49-1.84(m, 8H) | Fumarate | | | |
| | (Fumarate) | 2750 | 1695 | 1.95-2.05(m, 2H), 2.31-2.37(m, 2H) | | C | H | N |
| | | 1640 | 1605 | 2.37-2.51(m, 1H), 3.01-3.05(m, 2H) | Calc. | 62.64 | 6.16 | 7.56 |
| | | 1490 | 1430 | 3.87-3.92(m, 4H) | Obsd. | 62.29 | 6.17 | 7.56 |
| | | 1360 | 1320 | 4.70-4.73(m, 1H), 6.77(d, 1H, J=8.6Hz) | | | | |
| | | 1240 | 1120 | 6.94(t, 1H, J=7.9Hz) | | | | |
| | | 1090 | 980 | 7.13-7.37(m, 5H) | | | | |
| | | 825 | 750 | 8.26(d, 1H, J=7.9Hz) | | | | |
| 36 | 151-152° C. | 2920 | 2750 | 1.33-1.44(m, 2H), 1.50-1.84(m, 8H) | HCl salt ¼ H$_2$O | | | |
| | (HCl salt) | 1695 | 1640 | 1.98-2.07(m, 4H), 2.37(t, 2H, J=7.9Hz) | | C | H | N |
| | | 1600 | 1445 | 2.43-2.53(m, 1H), 2.99(s, 4H) | Calc. | 70.10 | 7.58 | 6.29 |
| | | 1335 | 1310 | 3.03-3.07(m, 2H) | Obsd. | 70.26 | 7.49 | 6.29 |
| | | 1240 | 1180 | 4.00(t, 2H, J=7.3Hz) | | | | |
| | | 1090 | 980 | 7.15-7.44(m, 8H) | | | | |
| | | 885 | 750 | 7.97(dd, 1H, J=1.3Hz&7.3Hz) | | | | |
| | | 695 | | | | | | |
| 37 | 175-178° C. | 2920 | 2750 | 1.35-1.44(m, 2H) | HCl salt | | | |
| | (HCl salt) | 1690 | 1640 | 1.53-1.84(m, 8H) | | C | H | N |
| | | 1595 | 1485 | 1.97-2.05(m, 2H), 2.34-2.40(m, 2H) | Calc. | 65.68 | 6.78 | 5.89 |
| | | 1440 | 1335 | 2.43-2.51(m, 1H), 2.99(s, 4H) | Obsd. | 65.60 | 6.95 | 5.84 |
| | | 1310 | 1240 | 3.03-3.07(m, 2H) | | | | |
| | | 1180 | 1085 | 3.97-4.02(m, 2H) | | | | |
| | | 1005 | 980 | 7.13-7.45(m, 7H) | | | | |
| | | 880 | 820 | 7.97(dd, 1H, J=1.3Hz&7.9Hz) | | | | |
| | | 750 | 705 | | | | | |

The pharmacological test results will now be explained.

(I) AFFINITY TO σ-receptor

The affinities of the present compounds to the δ-receptor were determined according to a method described in the "Molecular Pharmacology," Vol. 32, 772-784 (1987).

That is, 50 mM of a Tris-HCl (pH=7.7) buffer solution was added to all of the cerebra, other than the cerebellum, of Wistar male rats, followed by homogenizing for 30 minutes in a Polytson® and then centrifugally separating same at 35000 G for 10 minutes. To the resultant precipitate was added the same buffer solution as used above, and the homogenizing and the centrafugalization were repeated. This procedure was repeated once more, and to the final precipitate was added a 50 mM Tris -HCl (pH=8.0) buffer solution and the receptor having a binding capability. In the binding experiments, 3nM [$^3$H] propyl-3-(3-hydroxyphenyl) piperidine (i.e., [$^3$H]3PPP) was used, and as a non-specific ligand, 1 μM haloperidol was used. After incubation at 25° C. for 90 minutes, the bound ligand was recovered by filtration and the determination was carried out. The filter used was a Whatmen GF/B filter treated with 0.5% polyethylene imine.

All of the present compounds exhibit strong activities on the order of μM or less. The receptor binding capabilities of the typical compounds are shown in Table III.

TABLE III

| Affinity to δ-Receptor | |
|---|---|
| Example No. | IC$_{50}$ (nM) |
| 1 | 14.2 |
| 2 | 11.7 |
| 4 | 9.22 |
| 5 | 18.7 |
| 8 | 6.61 |
| 9 | 4.73 |
| 12 | 12.1 |
| 14 | 17.8 |
| 17 | 4.00 |
| 18 | 14.1 |
| 19 | 16.1 |
| 21 | 13.7 |
| 22 | 3.74 |
| 23 | 6.40 |
| 26 | 10.9 |
| 27 | 10.6 |
| 28 | 8.02 |
| 29 | 10.3 |
| 30 | 4.73 |
| 31 | 7.82 |
| 32 | 3.95 |
| 33 | 17.6 |
| 36 | 3.62 |
| 37 | 8.91 |

(II) Inhibitory Activity Against Locomotor Hyperactivity Induced by Anfoneric Acid The inhibitory activity against locomotor hyperactivity induced by amfoneric acid of the present compounds were determined according to a method described in the "Journal of Pharmacology & Experimental Therapeuties," Vol. 239, 124-131 (1986) by R. T. Matthews et al.

That is, to a ddy male mouse having a body weight of about 25g, were simultaneously administered amfoneric acid (2.5 mg/kg, subcutaneous administration) and the present compound (intraperitoneal administration), and the amount of movement was determined using an apparatus for determining the amount of movement of a mouse. The amount of movement was determined over 100 minutes, and the test of significance thereof was effected for the total count number for 100 minutes by a Manwhitnee test. The value was indicated as the inhibition rate based, as a control, upon the group to which 2.5 mg/kg of amfoneric acid was subcutaneously administered.

The results are shown in Table IV.

TABLE IV

| | Inhibitory activity against locomotor hyperativity induced by anfoneric acid |
|---|---|
| Example No. | Inhibition Rate (%) (mg/kg Intraperitoneal administration) |
| 8 | 73%* (30) |
| 18 | 90%** (10), 65%* (1) |
| 19 | 53%* (10) |
| 22 | 52%* (10) |
| 26 | 65%** (10) |
| 29 | 60%** (10) |
| 30 | 70%* (30) |
| 37 | 74%* (10) |
| Control BMY14802 | 51%* (30) |

*0.05 > P > 0.01
**0.01 > P > 0.001

(III) Catalepsy

To ddy male mice having a body weight of about 25 g was intraperitoneally administered the present compound and the catalepsy was determined after 30, 60, 90, and 120 minutes therefrom. The score of the catalepsy was as follows.

The forelegs of the mouse were placed on an aupper edge of a 5.5 cm height box and the time until the more fulled its forelegs down from the box or the mouse jumped up onto the top of the box was measured and the score was determined based upon the following standard.

| Score | Condition |
|---|---|
| 0 | 15 sec or less |
| 1 | more than 15 sec but less than 30 sec |
| 2 | more than 30 sec but less than 60 sec |
| 3 | more than 60 sec |

The results are evaluated based upon the determined score as follows.

| Evaluation | Score |
|---|---|
| − | less than 1 |
| + | more than 1 but less than 2 |
| ++ | more than 2 but less than 3 |

The results of the typical compounds are shown in Table V.

TABLE V

| | Catalepsy |
|---|---|
| Example No. | Catalepsy (mg/kg Intraperitoneal administration) |
| 8 | − (30) |
| 18 | − (10) |
| 19 | − (20) |
| 21 | − (30) |
| 26 | − (30) |
| 29 | − (30) |
| 30 | − (30) |
| 31 | − (30) |
| 37 | − (30) |
| Control (Haloperidol) | ++ (0.1) |

We claim:
1. A compound of the formula (I):

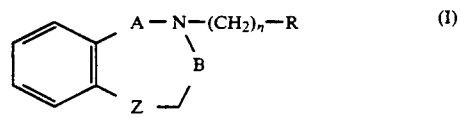

wherein A and B are both carbonyl groups or one thereof represents a methylene group and the other represents a carbonyl group; Z represents an oxygen atom, a sulfur atom, an imino group which may be substituted with a lower alkyl group or a methylene group; n is an integer of 2 to 6; and R represents a group having the following formula:

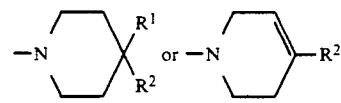

wherein $R^1$ represents a hydrogen atom or a hydroxy group; $R^2$ represents a phenyl group which may be substituted with halogen atoms, or pyridyl group; or a pharmacologically acceptable salt thereof.

2. A compound as claimed in claim 1, wherein the substituted imino group in Z is a $C_1$-$C_5$ alkylimino group.

3. A compound as claimed in claim 1, wherein A represents a carbonyl group and B represents a carbonyl group or methylene group.

4. A compound as claimed in claim 1, wherein R represents the following formula:

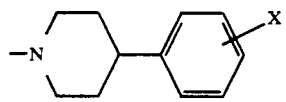

wherein X represents a hydrogen atom or a halogen atom.

5. A psychopharmaceutical composition comprising a compound of the formula (I) according to claim 1 or a pharmacologically acceptable salts thereof, as an effective component, and a carrier thereof.

6. A psychopharmaceutical composition as claimed in claim 5, wherein said compound of the formula (I) is at least one compound selected from the group consisting of 4-(4-(4-phenyl)-1-piperidinyl)butyl-2,3,4,5-tetrahydro-1,4-benzodiazepine-3,5-dione, 4-(5-(4-phenyl)-1-piperidinyl)pentyl-2,3,4,5-tetrahydro-1,4-benzoxazepin- 5-one and 2-(5-(4-(chlorophenyl)-1-piperidinyl)pentyl-1,3,4,5-tetrahydro-2-benzazepine-1,3-dione.

7. A psychopharmaceutical composition comprising a compound of the formula (I) according to claim 2 or a pharmacologically acceptable salt thereof, as an effective component, and a carrier thereof.

8. A psychopharmaceutical composition comprising a compound of the formula (I) according to claim 3 or a pharmacologically acceptable salt thereof, as an effective component, and a carrier thereof.

9. A psychopharmaceutical composition comprising a compound of the formula (I( according to claim 4 or a pharmacologically acceptable salt thereof, as an effective component, and a carrier thereof.

10. A psychopharmaceutical composition according to claim 7, wherein the compound of the formula (I) is at least one compound selected from the group consisting of 4-(4-(4-phenyl)-1-piperidinyl)butyl-2,3,4,5-tetrahydro-1,4-benzodiazepine-3,5-dione, 4-(5-4-phenyl)-1-piperidinyl)pentyl-2,3,4,5-tetrahydro-1,4-benzoxazepin-5-one and 2-(5-(4-(chlorophenyl)-1-piperidinyl)pentyl-1,3,4,5-tetrahydro-2-benzazepine-1,3-dione.

11. A psychopharmaceutical composition according to claim 8, wherein the compound of the formula (I) is at least one compound selected from the group consisting of 4-(4-(4-phenyl)-1-piperidinyl)butyl-2,3,4,5-tetrahydro-1,4-benzodiazepine-3,5-dione, 4-(5-4-phenyl)-1-piperidinyl)pentyl-2,3,4,5-tetrahydro-1,4-benzoxazepin-5-one and 2-(5-(4-(chlorophenyl)-1-piperidinyl)pentyl-1,3,4,5-tetrahydro-2-benzazepine-1,3-dione.

12. A psychopharmaceutical composition according to claim 9, wherein the compound of the formula (I) is at least one compound selected from the group consisting of 4-(4-(4-phenyl)-1-piperidinyl)butyl-2,3,4,5-tetrahydro-1,4-benzodiazepine-3,5-dione, 4-(5-4-phenyl)-1-piperidinyl)pentyl-2,3,4,5-tetrahydro-1,4-benzoxazepin-5-one and 2-(5-(4-(chlorophenyl)-1-piperidinyl)pentyl-1,3,4,5-tetrahydro-2-benzazepine-1,3-dione.

* * * * *